United States Patent
Vogel et al.

(10) Patent No.: US 10,774,356 B2
(45) Date of Patent: Sep. 15, 2020

(54) TRANSAMINASES

(71) Applicant: C-LEcta GmbH, Leipzig (DE)

(72) Inventors: Andreas Vogel, Leipzig (DE); Daniel Schwarze, Jena (DE); Rico Czaja, Leipzig (DE); Sally Bayer, Leipzig (DE); Sebastian Bartsch, Leipzig (DE)

(73) Assignee: C-LEcta GmbH, Leipzig (DE)

( * ) Notice: Subject to any disclaimer, the term of this patent is extended or adjusted under 35 U.S.C. 154(b) by 0 days.

(21) Appl. No.: 15/735,170

(22) PCT Filed: Jun. 10, 2016

(86) PCT No.: PCT/EP2016/063393
§ 371 (c)(1),
(2) Date: Dec. 9, 2017

(87) PCT Pub. No.: WO2016/198665
PCT Pub. Date: Dec. 15, 2016

(65) Prior Publication Data
US 2019/0078130 A1    Mar. 14, 2019

(30) Foreign Application Priority Data

Jun. 12, 2015 (EP) .................................... 15171924

(51) Int. Cl.
C12P 13/00 (2006.01)
C12P 7/26 (2006.01)
C12N 9/10 (2006.01)
C12P 41/00 (2006.01)

(52) U.S. Cl.
CPC .......... *C12P 41/006* (2013.01); *C12N 9/1096* (2013.01); *C12P 7/26* (2013.01); *C12P 13/001* (2013.01); *C12Y 206/01* (2013.01)

(58) Field of Classification Search
CPC ........ C12N 9/1096; C12P 7/26; C12P 41/006; C12P 13/001; C12Y 206/01
See application file for complete search history.

(56) References Cited

U.S. PATENT DOCUMENTS 7,172,885 B2 * 2/2007 Pannuri ................ C12N 9/1096
435/128

FOREIGN PATENT DOCUMENTS

| EP | 2022852 B1 | 7/2017 |
| JP | 2007185133 A | 7/2007 |
| WO | 2004085624 A2 | 10/2004 |
| WO | 2006063336 A2 | 6/2006 |
| WO | 2010081053 A2 | 7/2010 |
| WO | 2011159910 A3 | 3/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
EBI accession No. GSP: ADS78319, Aminotransferase/mutase/deaminase enzyme #40, Dec. 30, 2004.
EBI accession No. GSP: AGH64081, Pseudomonas corrugata (S)-amine transaminase, SEQ ID 6, Jan. 10, 2008.
Neto, L.A., et al., Process Considerations for the Asymmetric Synthesis if ChiralAmines using—Transaminase, http://orbit.dtu.dk/flies/69085333/PhD_Thesis_Watson_Neto_final_print_version_thesis.pdf , Aug. 1, 2013, pp. 42-61.
Seo, et al., Exploring sequence space: Profile analysis and protein-ligand docing to screen [omega]-aminotransferases with expanded substrate specificity, Biotechnology Journal, Apr. 8, 2008, vol. 3, No. 5, pp. 676-686.
F. William Studier, Protein Expression and Purification, (2005), vol. 41, pp. 207-234.
S. Schatzle et al., Rapid and Sensitive Kinetic Assay for Characterization of ω-Transaminases, Anal.Chem., (2009), vol. 81, No. 19, pp. 8244-8248.
Stephen F. Altschul; John C. Wootton; E. Michael Gertz; Richa Agarwala;Aleksandr Morgulis; Alejandro A. Schaffer; Yi-Kuo Yu, "Protein database searchesusing compositionally adjusted substitution matrices", FEBS J., (2005), vol. 272, pp. 5101-5109.
Stephen F. Altschul; Thomas L. Madden; Alejandro A. Schaffer; Jinghui Zhang;Zheng Zhang; Webb Miller; David J. Lipman, "Gapped BLAST and PSI-BLAST: a new generation of protein database search programs", Nucleic Acids Res., (1997), vol. 25, pp. 3389-3402.

* cited by examiner

*Primary Examiner* — Ganapathirama Raghu
(74) *Attorney, Agent, or Firm* — Agris & Von Natzmer, LLP; Joyce Von Natzmer

(57) ABSTRACT

The invention relates to transaminases and their use. The ATAs according to the invention are particularly useful for catalyzing the conversion of amines to ketones and/or vice versa. Preferably, the transaminase (ATA) according to the invention comprises an amino acid sequence with at least 80% homology to SEQ ID NO:1, wherein the amino acid sequence is engineered compared to SEQ ID NO:1 such that it comprises at least a substitution selected from the group consisting of F255L, F255A, F255C, F255D, F255E, F255G, F255H, F255K, F255M, F255N, F255P, F255Q, F255R, F255S, F255T, F255V, F255W, and F255Y.

15 Claims, No Drawings
Specification includes a Sequence Listing.

TRANSAMINASES

CROSS-REFERENCE TO RELATED APPLICATIONS

This is the U.S. national stage of International application PCT/EP2016/063393, filed Jun. 10, 2016 designating the United States and claiming priority to European patent application EP 15171924.2, filed Jun. 12, 2015.

INCORPORATION OF SEQUENCE LISTING

The sequence listing was filed as a text file as part of International application PCT/EP2016/063393, filed Jun. 10, 2016 is hereby incorporated by reference. An extra copy of this text file named "eolf-seql.txt", which is 329 kilobytes (measured in MS-WINDOWS), dated Nov. 21, 2017 was downloaded from WIPO and is submitted herewith via the USPTO EFS system.

The application claims priority of EP15171924, filed on Jun. 12, 2015.

The invention relates to transaminases, also called aminotransferases, or more specifically to amine transaminases, in the following also abbreviated and referred to as "ATA". The ATAs according to the invention are particularly useful for catalyzing the conversion of amines to ketones and/or vice versa.

Transaminases are ubiquitous enzymes found in all kingdoms of life. Transaminases catalyze the transfer of an amino group from an amine donor molecule to an amine acceptor ketone molecule and vice versa. Transaminases are divided into six classes based on common structural features and sequence similarity (Steffen-Munsberg et al. 2015). So called "omega transaminases (ω transaminase) transfer amino groups that are more distant from a carboxylic group (e.g. in β, γ or δ position) and are often part of aminotransferase class-III family (mainly (S)-selective amine transaminases) or class-IV (mainly (R)-selective amine transaminases). For determining a protein's family membership, the InterPro web tool can be used on the European Bioinformatics Institute (EBI, UK) website Hunter et al., 2012).

The term "Amine transaminases" (ATA) describes transaminases, including omega transaminases, that allow for the conversion of amines independently from the presence or absence of carboxylic groups in the substrate, and predominantly are a subgroup of class III transaminases. Accordingly, the terminology of omega transaminase is misleading but often used in publications. ATAs are all enzymes which belong to the EC sub-subclass EC 2.6.1., as defined by the International Union of Biochemistry and Molecular Biology. As of the date of this invention, no specific EC serial number for transaminases primarily converting non-carboxyl substrates has been appointed, and ATAs often are referred to as EC 2.6.1.X whereas X stands for any enzyme classified in the sub-subclass EC 2.6.1., and as of the date of this invention for any figure from 1 to 107 (i.e. EC 2.6.1.1, EC 2.6.1.2, EC 2.6.1.3, . . . until EC 2.6.1.107). Other examples of members of the class III transaminases with different primary functions are acetylornithine aminotransferase (EC 2.6.1.11), ornithine aminotransferase (EC 2.6.1.13), omega-amino acid-pyruvate aminotransferase (EC 2.6.1.18), 4-aminobutyrate aminotransferase (EC 2.6.1.19), DAPA aminotransferase (EC 2.6.1.62), 2,2-dialkylglycine decarboxylase (EC 4.1.1.64), or glutamate-1-semialdehyde aminotransferase (EC 5.4.3.8).

The reaction of ATAs converts ketone substrates (A) into amine products (C) while simultaneously converting amino donor cosubstrates (B) into the corresponding ketone co-product (D):

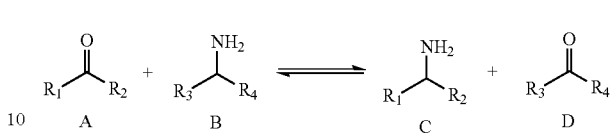

According to their stereoselectivity, two classes of ATAs have been distinguished: (S)-ATAs that preferentially catalyze formation of an (S)-amine from a keto group, and (R)-ATAs that preferentially catalyze formation of an (R)-amine from a keto group. However, this distinction in (S)-ATAs and (R)-ATAs can be misleading, as it depends on the nature of the substrate, namely the substituents of the keto group and their priority according to the rules of the CIP nomenclature (Cahn-Ingold-Prelog). Thus, a given ATA may be regarded as an (S)-ATA with respect to the conversion of one keto group, whereas the same ATA may be regarded as an (R)-ATA with respect to the conversion of another keto group.

The stereoselective synthesis of amine compounds, in particular of chiral amine compounds, is of outstanding interest for synthetic chemistry in particular in the pharmaceutical industry (Shaheer Malik et al, 2012), but also plays an important role in polymer chemistry (polyamides). Furthermore, ATAs can be applied for kinetic resolution of racemic amines.

The reaction that is catalyzed by ATAs is reversible (equilibrium reaction) and may undergo substrate or product inhibition, depending on the specific reaction equilibrium. In order to obtain industrially relevant amounts of a desired product, ATAs are required that catalyze the conversion of substrates with high specific activity. It may be required to bias the equilibrium reaction toward production of the desired amine compound by choosing optimal reaction conditions, resulting in high product yields over process time. Also other kinetic factors, such as substrate selectivity, $K_M$ and stereoselectivity may play an important role. Other relevant aspects may include but are not limited to diastereoselectivity, regioselectivity, inhibition by other factors (e.g. crude extract components, substrate contaminants or side products), and recombinant soluble expressability in suitable hosts.

Another important criterion in the industrial use of ATAs is a long process stability, which often correlates with a high stability at elevated temperatures, and good stability in solvents and/or at high concentrations of substrate and product, respectively. In industrial applications, process stability also may encompass chemical and physical stability, enzymatic activity in differing solvents (aqueous, non-aqueous environments, biphasic systems), and/or at a broad pH-range, e.g. from about pH 4 to about pH 11, and/or applicability with any solid supports or other processing technique.

For an efficient and economic use of ATAs in industrial applications it is desirable to employ ATAs with a high specific activity, high stereoselectivity, and high thermostability and high conversion.

Many of the currently known ATAs, however, do not possess sufficient thermostability, high conversion, or high stereoselective, and do not provide the desired (chiral) amine in sufficient yield.

Improvement of enzymes can be achieved by enzyme engineering. This technique involves the development of variants of a starting enzyme with improved properties (for review: S. Lutz, U. T. Bornscheuer, Protein Engineering Handbook, Wiley VCH, Weinheim, 2009).

The engineering of ATAs for improving stereoselectivity, thermostability or conversion has been described in the literature.

W Lima Afonso Neto et al., Technical University of Denmark, Phd Thesis, relates to process considerations for the asymmetric synthesis of chiral amines using transaminase.

JP 2007 185133 (GSP:AGH64081) relates to an aminotransaminase maintaining its enzyme activity under a high temperature condition. This aminotransaminase is encoded by a polynucleotide derived from *Pseudomonas corrugata* and having a specific base sequence. It is possible to produce the aminotransaminase by preparing transformed cells by using a vector containing the polynucleotide. Thereby, it is also possible to produce an optically active amino compound such as an optically active 1-benzyl-3-aminopyrrolidine, etc.

EP 2 022 852 relates to a method for producing an optically-active amine compound. The method is characterized by using a transaminase (A), an alpha-keto acid reductase (B), and an enzyme (C), each having specific properties, in an identical reaction system to convert a ketone compound into a corresponding optically-active amine compound in which a carbon atom with an amino group bonded thereto serves as an asymmetric center.

WO 2004/085624 (GSP:ADS78319) relates to methods of enzymatic detoxification of aminated toxins, e.g., mycotoxins, such as fumonisin. The reference provides methods to enzymatically detoxify plants, foods or feeds or any contaminated product or surface, including detoxification of mycotoxins, such as fumonisin, e.g., fumonisin B1 and fumonisin B2. The reference provides methods to prevent the contamination of plants, foods or feeds or any contaminated product or surface by application or a polypeptide having a deaminase activity. In one aspect, the reference relates to polypeptides having an aminotransferase, an aminomutase and/or a deaminase activity, polynucleotides encoding these enzymes, methods of making and using these polynucleotides and polypeptides.

WO 2006/063336 discloses thermostable omega-transaminases, particularly thermostable omega-transaminases which are said to have a high reaction rate and which are said to be tolerant to high concentrations of donor amine. The wildtype sequence of the ATA of *Arthrobacter citreus* is said to have a residue D268 (i.e. an aspartate residue in position 268), whereas for the purpose of the specification it is referred to a wildtype ATA of *Arthrobacter citreus* having a residue N268 (i.e. an asparagine in position 268).

WO 2010/081053 provides engineered transaminase enzymes having improved properties as compared to a naturally occurring wild-type transaminase enzyme. Also provided are polynucleotides encoding the engineered transaminase enzymes, host cells capable of expressing the engineered transaminase enzymes, and methods of using the engineered transaminase enzymes to synthesize a variety of chiral compounds.

WO 2011/159910 relates to engineered transaminase polypeptides which are said to have improved properties as compared to naturally occurring transaminases including the ability of converting the substrate, 3'-hydroxyacetophenone to (S)-3-(1-aminoethyl)-phenol in enantiomeric excess and high percentage conversion.

The ATAs of the prior art, however, are not satisfactory in every respect and there is a demand for improved ATAs having advantages compared to conventional ATAs, in particular with respect to high process stabilities at high temperatures for the industrial production of chiral amine products with good yields in high enantiomeric excess.

It is an object of the invention to provide ATAs that have advantages to the ATAs of the prior art.

This problem has been achieved by the subject-matter of the patent claims.

A first aspect of the invention relates to ATAs which are obtained from the ATA of SEQ ID NO:1, by engineering, but which are not identical to SEQ ID NO:1.

For the purpose of the specification, "engineered ATA" refers to an ATA differing from the specified wildtype sequence, e.g. the non-engineered ATA of SEQ ID NO:1. Engineering can mean substitution of an amino acid residue of the specified wildtype sequence by another amino acid residue. In addition, engineering can also mean deletion of an amino acid residue of the specified wildtype sequence, or insertion of an amino acid residue into the specified wildtype sequence, or substitution of an amino acid residue of the specified wildtype sequence by more than a single other amino acid residues.

In this regard, engineering means that one or more amino acids in a given position are substituted with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp Tyr, and Val. In a preferred embodiment, the substitution does not alter the sequence length, i.e. a single amino acid residue is replaced by another single amino acid residue. However, it is also possible to delete one or more amino acid residues without replacement and/or to insert one or more amino acid residues.

In one specific embodiment, the engineered ATA according to the invention is a fragment of at least 380 amino acid residues, more preferably at least 400 amino acid residues, more preferably at least 420 amino acid residues, more preferably at least 425 amino acid residues, more preferably at least 430 amino acid residues, more preferably at least 435 amino acid residues, more preferably at least 440 amino acid residues, more preferably at least 445 amino acid residues, and most preferably at least 446 amino acids residues of the polypeptide of SEQ ID NO:1. In this regard, "fragment" refers to a consecutive subsequence of the respective SEQ ID NO:1 but that is shortened at the N-terminus and/or the C-terminus.

In principle, a substitution in any position of an enzyme may be a conservative substitution where such amino acid is substituted with an amino acid of comparable characteristics (e.g. substitution of a hydrophobic amino acid with another hydrophobic amino acid). In addition, a substitution in any position of an enzyme may be a non-conservative substitution where such amino acid is substituted with an amino acid of other characteristics (e.g. substitution of a hydrophobic amino acid with a hydrophilic amino acid).

Preferred engineered ATAs in accordance with the invention comprise amino acid sequences of SEQ ID NO:2, 3 and 4, respectively. The relationship of SEQ ID NO:2, 3 and 4 as well as of SEQ ID NO:5, which was tested in the examples, to SEQ ID NO:1 is compiled in the table here below:

| Position | 25 | 48 | 164 | 195 | 242 | 245 | 255 | 268 | 328 | 409 | 424 | 436 |
|---|---|---|---|---|---|---|---|---|---|---|---|---|
| SEQ ID NO: 1 | Phe | Asp | Tyr | Pro | Ala | Ala | Phe | Asn | Val | Thr | Lys | Val |
| SEQ ID NO: 2 | Phe | Gly | Phe | Ser | Val | Thr | Leu | Ala | Val | Arg | Glu | Ala |
| SEQ ID NO: 3 | Phe | Asp | Tyr | Pro | Ala | Ala | Leu | Asn | Gly | Thr | Lys | Val |
| SEQ ID NO: 4 | Leu | Asp | Met | Pro | Ala | Ala | Leu | Asn | Val | Thr | Lys | Val |
| SEQ ID NO: 5 | Phe | Asp | Tyr | Pro | Ala | Ala | Leu | Asn | Val | Thr | Lys | Val |

Thus, compared to SEQ ID NO:1, the amino acid sequence of SEQ ID NO:2 has 10 mutations, the amino acid sequence of SEQ ID NO:3 has 2 mutations, the amino acid sequence of SEQ ID NO:4 has 3 mutations, and the amino acid sequence of SEQ ID NO:5 has 1 mutation.

Preferably, the engineered ATAs obtained from the ATA of SEQ ID NO:1 according to the invention are capable of catalyzing the conversion of a ketone substrate according to general formula (I) as defined below to an amine product according to general formula (II) as defined below; and/or the preferably concomitant conversion of (ii) an amine cosubstrate according to general formula (III) as defined below to a ketone coproduct according to general formula (IV) as defined below, or vice versa.

It has been surprisingly found that upon selective engineering of SEQ ID NO:1, the characteristics of the respective ATA can be further enhanced, and that ATA variants can be obtained that exhibit in comparison to the wildtype sequence of SEQ ID NO:1
  a further improved stereoselectivity, and/or
  a further increased thermostability, and/or
  a further increased conversion; and/or
  a shift in activity and/or conversion of substrate specificity.

It has been surprisingly found, that the ATA according to the invention shows superior thermostability, specific activity, and conversion under certain amine concentrations in comparison to other ATAs currently described.

In particular, it has surprisingly been found, that the ATA according to the invention converting a ketone substrate to an amine, or vice versa an amine to a ketone product has a high stability at mesophilic or high temperatures, measured as a high Tm(80%) value as described in Example 1 below. Preferably, the ATA according to the invention has a $T_m(80\%)$ value of at least 55° C., preferably of at least 56° C., preferably of at least 57° C., preferably of at least 58° C., preferably of at least 59° C., and most preferably of at least 60° C.

In particular, it furthermore has been surprisingly found, that the ATA according to the invention converting a ketone substrate to an amine product, or vice versa an amine substrate to a ketone product has a high specific activity under conditions of Transaminase Standard Assay as described in Example 1 below. In particular, the ATA according to the invention has a high specific activity for the conversion of racemic 1-phenylethan-1-amine (MBA) and pyruvate to 1-phenylethanone (acetophenone) and L-alanine as described below. Preferably, the specific activity of the ATA according to the invention in converting a ketone substrate to an amine, or vice versa an amine to a ketone product under conditions of Transaminase Standard Assay is at least 0.05 U/mg, 0.06 U/mg, 0.07 U/mg, 0.08 U/mg, 0.09 U/mg, 0.1 U/mg, 0.15 U/mg, 0.2 U/mg, 0.25 U/mg, 0.3 U/mg, 0.35 U/mg, 0.4 U/mg, 0.45 U/mg, 0.5 U/mg, preferably at least 0.6 U/mg, preferably at least 0.7 U/mg, preferably at least 0.8 U/mg, preferably at least 0.9 U/mg, preferably at least 1 U/mg, most preferably at least 1.1 U/mg.

In particular, it furthermore has been surprisingly found, that the ATA according to the invention converting a ketone substrate to an amine product, or vice versa an amine substrate to a ketone product shows high conversion of a substrate at certain concentrations of different amine donor co-substrates of industrial relevance. In particular, the ATA according to the invention shows high conversion properties at reaction conditions of relevant for preparative synthesis applications with the different amine donors, isopropylamine (IPA), racemic 1-phenylethan-1-amine (MBA) or racemic alanine, respectively with the substrate 4-phenyl-2-butanone (BA) as described in Example 1. In particular the ATA according to the invention is very efficient in conversion upon at the Condition A (50 mM BA, 100 mM IPA), the Condition B (50 mM BA, 200 mM rac. MBA), the Condition C (50 mM BA, 500 mM IPA), the Condition D (50 mM BA, 1000 mM rac. MBA), the Condition E (50 mM BA, 200 mM racemic alanine), the conditions Condition K (100 mM BA, 500 mM rac. MBA), the Condition L (200 mM BA, 500 mM rac. MBA), or Condition M (10 g/L BA, 900 mM IPA).

Preferably, the ATA according to the invention in converting a ketone substrate to an amine product, or vice versa an amine substrate to a ketone product under Transaminase Conversion Assay conditions (for details see experimental section) shows a conversion of
  at Condition A a conversion of at least 5%, preferably of at least 6%, preferably of at least 7%, preferably of at least 8%, preferably of at least 9%, preferably of at least 10%, preferably at least 10%, preferably at least 12.5%, preferably at least 15%, preferably at least 17.5%, preferably at least 20%, preferably at least 22.5%, preferably at least 25%, preferably at least 27.5%, preferably at least 30%, preferably at least 32.5%, and most preferably at least 33.7%; and/or
  at Condition B a conversion of at least 5%, preferably of at least 6%, preferably of at least 7%, preferably of at least 8%, preferably of at least 9%, preferably least 10%, preferably of at least 20%, preferably of at least 30%, preferably of at least 40%, preferably of at least 50%, preferably of at least 60%, preferably of at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, and most preferably at least 88.8; and/or
  at Condition C a conversion of at least 10%, preferably of at least 20%, preferably of at least 25%, preferably of at least 30%, preferably of at least 40%, preferably of at least 50%, preferably of at least 60%, preferably of at least 61%, preferably at least 62%, preferably at least 63%, preferably at least 64%, preferably at least 65%, preferably at least 66%, preferably at least 67%, preferably at least 68%, preferably at least 69%, preferably of at least 70%, and most preferably at least 70.7; and/or at Condition D a conversion of at least 10%, preferably of at least 20%, preferably of at least 30%, preferably of at least 40%, preferably of at least 41%, preferably at least 42%, preferably at least 43%, preferably at least 44%, preferably at least 45%, preferably at least 46%, preferably at least 47%, preferably at least 48%, preferably at least 49%, preferably of at least 50%, preferably of at least 51%, preferably at least 52%, preferably at least 53%, preferably at least 54%, and most preferably at least 54.8; and/or at Condition E a conversion of at least 0.5%, preferably of at least 1%, preferably of at least 1.5%, and most preferably of at least 1.6%; and/or at Condition K a conversion of at least 10%, preferably of at least 20%, preferably of at least 30%, preferably of at least 40%, preferably of at least 50%, preferably of at least 60%, preferably of at least 61%, preferably at least 62%, preferably at least 63%, preferably at least 64%, preferably at least 65%, preferably at least 66%, preferably at least 67%, preferably at least 68%, preferably at least 69%, preferably of at least 70%, preferably of at least 71%, preferably at least 72%, preferably at least 73%, and most preferably at least 74%; and/or at Condition L a conversion of at least 10%, preferably of at least 20%, preferably of at least 30%, preferably of at least 40%, preferably of at least 41%, preferably at least 42%, preferably at least 43%, preferably at least 44%, preferably at least 45%, preferably at least 46%, preferably at least 47%, preferably at least 48%, preferably at least 49%, preferably of at least 50%, preferably of at least 51%, preferably at least 52%, and most preferably at least 53% and/or at Condition M a conversion of at least 10%, preferably of at least 20%, preferably of at least 30%, preferably of at least 40%, preferably of at least 50%, preferably of at least 60%, preferably of at least 70%, preferably at least 71%, preferably at least 72%, preferably at least 73%, preferably at least 74%, preferably at least 75%, preferably at least 76%, preferably at least 77%, preferably at least 78%, preferably at least 79%, and most preferably at least 80%.

For the purpose of the specification, stereoselectivity is the property of a chemical reaction in which a single reactant forms an unequal mixture of stereoisomers during the non-stereospecific creation of a new stereocenter or during the non-stereospecific transformation of a pre-existing one. The selectivity typically arises from differences in steric effects and electronic effects in the mechanistic pathways leading to the different products. The enantiomeric excess (ee) of one chiral product over the other product obtained from an enzymatic reaction is a measure for the stereoselectivity of the enzyme, in particular of the ATA according to the invention:

$$\% \ ee = \frac{[\text{product}(chirality1)] - [\text{product}(chirality2)]}{[\text{product}(chirality1)] + [\text{product}(chirality2)]}.$$

The enantiomeric excess (expressed in percent) is calculated as the difference between the quantity of two products with differing chirality (product(chirality 1), product(chirality2)) expressed as absolute value divided by the sum of the concentration of both products, multiplied by 100. Preferably, the conversion of a substrate into a chiral product under catalysis of the ATA according to the invention provides the desired chiral product with an enantiomeric excess of at least 50% ee, more preferably at least 60% ee, more preferably at least 65% ee, more preferably at least 70% ee, more preferably at least 75% ee, still more preferably at least 80% ee, still more preferably at least 85% ee, still more preferably at least 90% ee, yet more preferably at least 91% ee, yet more preferably at least 92% ee, yet more preferably at least 93% ee, yet more preferably at least 94% ee, yet more preferably at least 95% ee, yet more preferably at least 96% ee, even more preferably at least 97% ee, most preferably at least 98% ee, and in particular at least 99% ee, and in particular at least 99.9% ee.

An improved stereoselectivity according to the invention relates to an enantiomeric excess of the product provided by means of an engineered ATA which is higher than the enantiomeric excess of the product provided by means of the non-engineered ATA of SEQ ID NO:1. Preferably, the enantiomeric excess provided by an engineered ATA according to the invention is increased by at least 0.1% ee, at least 0.5% ee, at least 1% ee, at least 3% ee, at least 5% ee, at least 7% ee, at least 9% ee, at least 11% ee, at least 13% ee, at least 15% ee, at least 17% ee, at least 19% ee, at least 21% ee, at least 23% ee, at least 25% ee, at least 27% ee, at least 29% ee, at least 31% ee, at least 32% ee, at least 33% ee, at least 34% ee, at least 35% ee, at least 36% ee, at least at least 37% ee, at least 38% ee, at least 39% ee, at least 40% ee, at least 41% ee, at least 42% ee, at least 43% ee, at least 44% ee, at least 45% ee, at least 46% ee, at least 47% ee, at least 48% ee, at least 49% ee, at least 50% ee, at least 55% ee, or at least 60% ee, at least 65% ee, at least 70% ee, at least 75% ee, at least 80% ee, at least 85% ee, at least 90% ee, at least 95% ee, at least 97% ee, at least 98% ee, at least 99% ee, or at least 99.5% ee and in particular at least 99.9% ee compared to the non-engineered ATA of SEQ ID NO:1 for a given substrate. The improved stereoselectivity may also mean that the engineered ATA does have a certain stereoselectivity towards the desired chiral product, whereas the non-engineered ATA has no significant stereoselectivity towards said chiral product. The improved stereoselectivity may also mean that the engineered ATA has a certain stereoselectivity towards one desired chiral product, whereas the non-engineered ATA has a stereoselectivity towards the reverse chiral product, e.g. the engineered ATA has a stereoselectivity for building an (R)-amine while the non-engineered ATA has a stereoselectivity for the (S)-amine and vice versa.

For the purpose of the specification, thermostability is the property of an enzyme to retain enzymatic activity upon incubation at high temperatures for a given time. The enzyme activity thereby can be determined at any assay conditions. For the purpose of this invention, the thermostability is expressed as Tm(80%) value, indicating the temperature at which an enzyme retains 80% of its in initial enzyme activity upon incubation in a given buffer system for 15 minutes at said temperature.

The thermostability of an ATA according to the invention, preferably the thermostability of the wild type ATA of SEQ ID NO:1 or an engineered ATA according to this invention, is preferably determined by incubation of the ATA containing crude extract for 15 minutes at several given temperatures in a PCR cycler. One sample of each ATA crude extract is incubated for 15 minutes in ice as a reference. Afterwards all crude extracts are incubated on ice for 30 minutes. Insoluble proteins are separated by centrifugation and the supernatant is analyzed regarding its remaining ATA activity in the Transaminase Standard Assay as described in Example 1 monitoring the conversion of 1-phenylethan-1-amine (MBA) and pyruvate to 1-phenylethanone (Acetophenone) and L-alanine.

An improved thermostability according to the invention relates to a higher Tm(80%) value of an engineered ATA in comparison to the non-engineered ATA of SEQ ID NO:1. Preferably, the Tm(80%) value is increased by at least 1° C., at least 2° C., at least 3° C., at least 4° C., at least 5° C., at least 6° C., at least 7° C., at least 8° C., at least 9° C., at least 10° C., at least 11° C., at least 12° C., at least 13° C., at least 14° C., at least 15° C., at least 16° C., at least 17° C., at least 18° C., at least 19° C., at least 20° C., at least 21° C., at least 22° C., at least 23° C., at least 24° C., at least 25° C., and most preferably at least 30° C. compared to the non-engineered ATA of SEQ ID NO:1.

For the purpose of the specification, the conversion of an enzyme according this invention is the yield of a given product after a given time in a reaction involving the enzyme. For the purpose of this invention, the conversion rate is expressed as X % conversion after a given time using 4-phenyl-2-butanone as substrate together with isopropylamine (IPA) or (S)-1-phenylethan-1-amine (S-MBA) as amine donor to the corresponding product 1-methyl-3-phenylpropylamine and acetone or 1-phenylethanone (acetophenone) under a respective condition. While the conversion of a given ATA according this invention may deviate depending on different substrates used, the improved conversion of an engineered ATA according to this invention can be determined in either of the Transaminase Conversion Assay conditions Condition A, Condition B, Condition C, Condition D, Condition E, Condition K, Condition L, and/or Condition M as described above and in Example 1.

An improved conversion according to the invention relates to a conversion of an engineered ATA which is higher than the conversion of the non-engineered ATA of SEQ ID NO:1 under a respective Condition. Preferably, the conversion under any condition is at least 0.1%, preferably at least 0.2%, at 0.3%, at least 0.4%, at least 0.5%, at least 1%, at least 1.5%, at least 2.5%, at least 5%, at least 7.5%, more preferably at least 10%, more preferably at least 12.5%, more preferably at least 15%, more preferably at least 17.5%, more preferably at least 20%, more preferably at least 22.5%, more preferably at least 25%, more preferably at least 27.5%, more preferably at least 30%, 35%, preferably at least 40%, preferably at least 45%, preferably at least 46%, preferably at least 47%, preferably at least 48%, preferably at least 49%, preferably at least 50%, preferably at least 51%, preferably at least 52%, preferably at least 53%, preferably at least 54%, preferably at least 55%, preferably at least 56%, preferably at least 57%, preferably at least 58%, preferably at least 59%, preferably at least 60%, preferably at least 61%, preferably at least 62%, preferably at least 63%, preferably at least 64%, preferably at least 65%, preferably at least 66%, preferably at least 67%, preferably at least 68%, preferably at least 69%, preferably at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80% preferably at least 81%, preferably at least 82%, preferably at least 83%, preferably at least 84%, preferably at least 85%, preferably at least 86%, preferably at least 87%, preferably at least 88%, preferably at least 89%, preferably at least 90% preferably at least 91%, preferably at least 92%, preferably at least 93%, preferably at least 94%, preferably at least 95%, preferably at least 96%, preferably at least 97%, preferably at least 98%, most preferably at least 99%, higher than the conversion of the non-engineered ATA of SEQ ID NO:1.

In preferred embodiments, the amino acid sequence is engineered compared to SEQ ID NO:1 in at least two positions, or in at least three positions, or in at least four positions, or in at least five positions, or in at least six positions, or in at least seven positions, or in at least eight positions, or in at least nine positions, or in at least ten positions.

Preferably, the amino acid sequence of SEQ ID NO:1 is engineered in at least one or more positions preferably by 1 to 20 residue changes, even more preferably by 1 to 15 residue changes, even more preferably by 1 to 11 residue changes, preferably including changes at one or more of the following positions of SEQ ID NO:1: V13, E15, M22, F25, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, F255, N268, V271, L272, S302, K314, V328, K358, E362, Y363, H375, L387, T409, H410, K424, G434, V436, M437, T440, R442, and S450.

Preferably, the amino acid sequence of SEQ ID NO:1 is engineered in at least one or more positions preferably by 1 to 20 residue changes, even more preferably by 1 to 15 residue changes, even more preferably by 1 to 11 residue changes, preferably including changes at one or more of the following positions of SEQ ID NO:1: V13, E15, M22, F25, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, F255, N268, V271, L272, S302, K314, V328, K358, E362, Y363, H375, L387, T409, H410, K424, G434, V436, M437, T440, R442, and S450 with substitution of any of the amino acids of these positions with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp Tyr, and Val.

In preferred embodiments, the amino acid sequence of SEQ ID NO:1 is engineered such that it comprises at least one or more substitutions selected from the group consisting of in position V13 substitution to V13L;
in position E15 substitution to E15R
in position M22 substitution to M22F, M22C, M22V, M22L, M22A, or M22W;
in position F25 substitution to F25L;
in position P35 substitution to P35L or P35I;
in position T39 substitution to T39Y;
in position D48 substitution to D48G;
in position T50 substitution to T50R, T50N, or T50H;
in position R51 substitution to R51K;
in position N57 substitution to N57S;
in position L59 substitution to L59F, L59W, L59V, L59A, L59S, or L59G;
in position Y60 substitution to Y60A, Y60I, Y60L, Y60F, or Y60V;
in position A73 substitution to A73N;
in position A74 substitution to A74P;
in position E77 substitution to E77G;
in position L79 substitution to L79M;
in position T88 substitution to T88V, T88A, T88G, T88L, or T88Y;
in position Y93 substitution to Y93T or Y93N;
in position V115 substitution to V115I;
in position T120 substitution to T120S;

in position L140 substitution to L140K;
in position H146 substitution to H146Y, H146D, or H146S;
in position D147 substitution to D147S;
in position Y148 substitution to Y148F, Y148S, or Y148G;
in position W151 substitution to W151A, W151I, W151F, W151Y, or W151S;
in position L161 substitution to L161A, L161F, L161M, L161Y, L161I, or L161Q;
in position Y164 substitution to Y164F or Y164M;
in position P195 substitution to P195S;
in position E237 substitution to E237S, E237A, or E237D;
in position A242 substitution to A242V, A242Y, or A242G;
in position G243 substitution to G243A or G243I;
in position S244 substitution to S244A, S244G, S244I, or S244L;
in position A245 substitution to A245T;
in position F255 substitution to F255L;
in position N268 substitution to N268A;
in position V271 substitution to V271A;
in position L272 substitution to L272I or L272A;
in position S302 substitution to S302G;
in position K314 substitution to K314E;
in position V328 substitution to V328G;
in position K358 substitution to K358E;
in position E362 substitution to E362R;
in position Y363 substitution to Y363F;
in position H375 substitution to H375F;
in position L387 substitution to L387V, L387I, L387F, L387Y, L387T, L387A, or L387C;
in position T409 substitution to T409R;
in position H410 substitution to H410K or H410E;
in position K424 substitution to K424E;
in position G434 substitution to G434A, G434V, G434L, G434Y, G434T, or G434C;
in position V436 substitution to V436A;
in position M437 substitution to M437T, M437C, M437F, M437V, M437Y, or M437A;
in position T440 substitution to T440H, T440S, or T440N;
in position R442 substitution to R442V, R442S, R442A, R442L, or R442C;
in position S450 substitution to S450N.

More preferably, the amino acid sequence of SEQ ID NO:1 is engineered in at least one or more positions of SEQ ID NO:1 selected from the group comprising positions M22, F25, T39, D48, T50, Y60, A73, V93, H146, L161, Y164, P195, A242, G243, S244, A245, F255, N268, V328, T409, K424, G434, V436, M437, T440, and R442.

Even more preferably, the amino acid sequence of SEQ ID NO:1 is engineered in at least one or more positions of SEQ ID NO:1 selected from the group comprising positions F25, D48, Y164, P195, A242, A245, F255, N268, V328, T409, K424, and V436.

Most preferably, the amino acid sequence of SEQ ID NO:1 is engineered in the positions
D48, Y164, P195, A242, A245, F255, N268, T409, K424, and V436, preferably D48G, Y164F, P195S, A242V, A245T, F255L, N268A, T409R, K424E, and V436A; and or/
F255, and V328, preferably F255L and V328G; and/or
F25, Y164, and F255, and preferably F25L, Y164M, and F255L.

Preferably, the transaminase (ATA) according to the invention comprises an amino acid sequence with at least 80% homology to SEQ ID NO:1, wherein the amino acid sequence is engineered compared to SEQ ID NO:1 such that it comprises at least a substitution selected from the group consisting of F255L, F255A, F255C, F255D, F255E, F255G, F255H, F255K, F255M, F255N, F255P, F255Q, F255R, F255S, F255T, F255V, F255W, and F255Y.

In the meaning of this invention, the homology is preferably calculated as identity using BLASTP (Stephen F. Altschul, Thomas L. Madden, Alejandro A. Schaffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schaffer, and Yi-Kuo Yu (2005) "Protein database searches using compositionally adjusted substitution matrices." FEBS J. 272:5101-5109), preferably using version BLASTP 2.2.29+, preferably using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 100; Short queries: Automatically adjust parameters for short input sequences; Expect threshold: 10; Word size: 3; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none.

The ATA according to the invention comprises such an amino acid sequence with a defined homology to the amino acid sequence of SEQ ID NO:1. Further definitions according to the invention refer to a homology with respect to SEQ ID NO: 2, 3 and 4, respectively. This means that the ATA according to the invention may comprise said amino acid sequence as a subsequence of its overall amino acid sequence, or that the ATA according to the invention may essentially consist of said amino acid sequence. When the ATA according to the invention comprises said amino acid sequence as a subsequence of its overall amino acid sequence, said overall amino acid sequence may be extended, i.e. may comprise additional amino acid residues, at the N-terminus and/or at the C-terminus of said subsequence. Such extension may be advantageous, for example, when the ATA is to be immobilized on a solid support, e.g. for purification purposes.

In a particularly preferred embodiment, the amino acid sequence is engineered compared to SEQ ID NO:1 in at least two positions such that it comprises the substitutions F255L and N268A.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of N268A, N268C, N268D, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of N268A, N268C, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of N268A, N268F, N268H, N268I, N268K, N268L, N268M, N268N, N268P, N268Q, N268R, N268V, N268W.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of N268A, N268F, N268H, N268I, N268V, preferably N268A.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) the substitution N268A.

Preferably, the amino acid sequence is engineered compared to SEQ ID NO:1 in at least two positions such that it comprises
(i) the substitution F255L; and
(ii) a substitution selected from the group consisting of N268A, N268C, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:1 in at least two positions such that it comprises
(i) the substitution F255L; and
(ii) a substitution selected from the group consisting of N268A, N268F, N268H, N268I, N268K, N268L, N268M, N268N, N268P, N268Q, N268R, N268V, N268W.

Preferably, the amino acid sequence is engineered compared to SEQ ID NO:1 in at least two positions such that it comprises
(i) the substitution F255L; and
(ii) a substitution selected from the group consisting of N268A, N268F, N268H, N268I, N268V, preferably N268A.

In another preferred embodiment, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of F25A, F25C, F25D, F25E, F25G, F25H, F25I, F25K, F25L, F25M, F25N, F25P, F25Q, F25R, F25S, F25T, F25V, F25W, and F25Y.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of F25A, F25C, F25G, F25H, F25I, F25L, F25M, F25N, F25Q, F25R, F25S, F25T, F25V.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) the substitution F25L.

Preferably, the amino acid sequence is engineered compared to SEQ ID NO:1 in at least two positions such that it comprises
(i) the substitution F255L; and
(ii) a substitution selected from the group consisting of F25A, F25C, F25D, F25E, F25G, F25H, F25I, F25K, F25L, F25M, F25N, F25P, F25Q, F25R, F25S, F25T, F25V, F25W, and F25Y.

Preferably, the amino acid sequence is engineered compared to SEQ ID NO:1 in at least two positions such that it comprises
(i) the substitution F255L; and
(ii) a substitution selected from the group consisting of F25A, F25C, F25G, F25H, F25I, F25L, F25M, F25N, F25Q, F25R, F25S, F25T, F25V.

Preferably, the amino acid sequence is engineered compared to SEQ ID NO:1 in at least two positions such that it comprises
(i) the substitution F255L; and
(ii) the substitution F25L.

In still another preferred embodiment, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of V328A, V328C, V328D, V328E, V328F, V328G, V328H, V328I, V328K, V328L, V328M, V328N, V328P, V328Q, V328R, V328S, V328T, V328W, and V328Y.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) a substitution selected from the group consisting of V328A, V328C, V328G, V328P, V328S, and V328T.

Preferably, the amino acid sequence is engineered compared to SEQ ID NO:1 in at least two positions such that it comprises
(i) a substitution selected from the group consisting of F255L, F255A, F255C, F255D, F255E, F255G, F255H, F255K, F255M, F255N, F255P, F255Q, F255R, F255S, F255T, F255V, F255W, and F255Y; and
(ii) the substitution V328G.

Preferably, the amino acid sequence is engineered compared to SEQ ID NO:1 in at least two positions such that it comprises
(i) the substitution F255L; and
(ii) a substitution selected from the group consisting of V328A, V328C, V328D, V328E, V328F, V328G, V328H, V328I, V328K, V328L, V328M, V328N, V328P, V328Q, V328R, V328S, V328T, V328W, and V328Y.

Preferably, the amino acid sequence is engineered compared to SEQ ID NO:1 in at least two positions such that it comprises
(i) the substitution F255L; and
(ii) a substitution selected from the group consisting of V328A, V328C, V328G, V328P, V328S, and V328T.

Preferably, the amino acid sequence is engineered compared to SEQ ID NO:1 in at least two positions such that it comprises
(i) the substitution F255L; and
(ii) the substitution V328G.

In preferred embodiments, the amino acid sequence is additionally engineered compared to SEQ ID NO:1 in at least one further position selected from the group consisting of D48, Y60, Y164, P195, A242, A245, T409, K424, and V436.

In preferred embodiments, the amino acid sequence is additionally engineered compared to SEQ ID NO:1 in at least one further positions by an amino acid residue selected from the group consisting of V13, E15, M22, P35, T39, T50, R51, N57, L59, A73, A74, E77, L79, T88, V93, V115, T120, L140, H146, D147, Y148, W151, L161, E237, G243, S244, V271, L272, S302, K314, K358, E362, Y363, H375, L387, H410, G434, M437, T440, R442, and S450.

In preferred embodiments, the amino acid sequence is additionally engineered compared to SEQ ID NO:1 in at least one further position such that it comprises a substitution selected from the group consisting of V13L, E15R, M22F, M22C, M22V, M22L, M22A, M22W, P35L, P35I, T39Y, D48G, T50R, T50N, T50H, R51K, N57S, L59F, L59W, L59V, L59A, L59S, L59G, Y60A, Y60I, Y60L, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161F, L161M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, S302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

Preferably, the amino acid sequence is engineered compared to SEQ ID NO:1 in
(i) at least two positions such that it comprises the substitutions F255L as well as N268A; or F255L as well as V328G; or F25L as well as F255L; and
(ii) at least one further position selected from the group consisting of V13, E15, M22, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, V271, L272, S302, K314, K358, E362, Y363, H375, L387, T409, H410, K424, G434, V436, M437, T440, R442, and S450.

Preferably, the amino acid sequence is engineered compared to SEQ ID NO:1 in
(i) at least two positions such that it comprises the substitutions F255L as well as N268A; or F255L as well as V328G; or F25L as well as F255L; and
(ii) at least one further position such that it comprises a further substitution selected from the group consisting of V13L, E15R, M22F, M22C, M22V, M22L, M22A, M22W, P35L, P35I, T39Y, D48G, T50R, T50N, T50H, R51K, N57S, L59F, L59W, L59V, L59A, L59S, L59G, Y60A, Y60I, Y60L, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161F, L161M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, S302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

While the above preferred embodiments have been defined compared to the amino acid sequence of SEQ ID NO:1, the following preferred embodiments are defined compared to the amino acid sequence of SEQ ID NO:5 differing from SEQ ID NO:1 only in the position 255, which is L255 instead of F255.

Preferably, the amino acid sequence of SEQ ID NO:5 is engineered in at least one or more positions of SEQ ID NO:5 selected from the group comprising positions M22, F25, T39, D48, T50, Y60, A73, V93, H146, L161, Y164, P195, A242, G243, S244, A245, L255, N268, V328, T409, K424, G434, V436, M437, T440, and R442.

Preferably, the amino acid sequence of SEQ ID NO:5 is engineered in at least one or more positions of SEQ ID NO:5 selected from the group comprising positions F25, D48, Y164, P195, A242, A245, L255, N268, V328, T409, K424, and V436.

Preferably, the amino acid sequence of SEQ ID NO:5 is engineered in the positions
D48, Y164, P195, A242, A245, N268, T409, K424, and V436, preferably D48G, Y164F, P195S, A242V, A245T, N268A, T409R, K424E, and V436A; and or/
V328, preferably V328G; and/or
F25 and Y164, and preferably F25L and Y164M.

Preferably, the transaminase (ATA) according to the invention comprises an amino acid sequence with at least 80% homology to SEQ ID NO:5, wherein the amino acid sequence is engineered compared to SEQ ID NO:5 such that it comprises at least a substitution selected from the group consisting of L255A, L255C, L255D, L255E, L255G, L255H, L255K, L255M, L255N, L255P, L255Q, L255R, L255S, L255T, L255V, L255W, and L255Y.

In a particularly preferred embodiment, the amino acid sequence is engineered compared to SEQ ID NO:5 in at least one position such that it comprises the substitution N268A.

Preferably, the amino acid sequence is engineered compared to SEQ ID NO:5 in at least two positions such that it comprises (i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of N268A, N268C, N268D, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of N268A, N268C, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of N268A, N268F, N268H, N268I, N268K, N268L, N268M, N268N, N268P, N268Q, N268R, N268V, N268W.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of N268A, N268F, N268H, N268I, N268V, preferably N268A.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) the substitution N268A.

Preferably, the amino acid sequence is engineered compared to SEQ ID NO:5 in at least one position such that it comprises a substitution selected from the group consisting of N268A, N268C, N268E, N268F, N268G, N268H, N268I, N268K, N268L, N268M, N268P, N268Q, N268R, N268S, N268T, N268V, N268W, and N268Y.

Preferably, the amino acid sequence is engineered compared to SEQ ID NO:5 in at one position such that it comprises a substitution selected from the group consisting of N268A, N268F, N268H, N268I, N268K, N268L, N268M, N268N, N268P, N268Q, N268R, N268V, N268W.

Preferably, the amino acid sequence is engineered compared to SEQ ID NO:5 in at least one position such that it comprises a substitution selected from the group consisting of N268A, N268F, N268H, N268I, N268V, preferably N268A.

In another preferred embodiment, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of F25A, F25C, F25D, F25E, F25G, F25H, F25I, F25K, F25L, F25M, F25N, F25P, F25Q, F25R, F25S, F25T, F25V, F25W, and F25Y.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of F25A, F25C, F25G, F25H, F25I, F25L, F25M, F25N, F25Q, F25R, F25S, F25T, F25V.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) the substitution F25L.

Preferably, the amino acid sequence is engineered compared to SEQ ID NO:5 in at least one position such that it comprises a substitution selected from the group consisting of F25A, F25C, F25D, F25E, F25G, F25H, F25I, F25K, F25L, F25M, F25N, F25P, F25Q, F25R, F25S, F25T, F25V, F25W, and F25Y.

Preferably, the amino acid sequence is engineered compared to SEQ ID NO:5 in at least one position such that it comprises a substitution selected from the group consisting of F25A, F25C, F25G, F25H, F25I, F25L, F25M, F25N, F25Q, F25R, F25S, F25T, F25V.

Preferably, the amino acid sequence is engineered compared to SEQ ID NO:5 in at least one position such that it comprises the substitution F25L.

In still another preferred embodiment, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of V328A, V328C, V328D, V328E, V328F, V328G, V328H, V328I, V328K, V328L, V328M, V328N, V328P, V328Q, V328R, V328S, V328T, V328W, and V328Y.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) a substitution selected from the group consisting of V328A, V328C, V328G, V328P, V328S, and V328T.

Preferably, the amino acid sequence is engineered compared to SEQ ID NO:5 in at least two positions such that it comprises
(i) a substitution selected from the group consisting of L255A, L255C, L255D, L255E, L255G, L255H, L255K, L255M, L255N, L255P, L255Q, L255R, L255S, L255T, L255V, L255W, and L255Y; and
(ii) the substitution V328G.

Preferably, the amino acid sequence is engineered compared to SEQ ID NO:5 in at least one position such that it comprises a substitution selected from the group consisting of V328A, V328C, V328D, V328E, V328F, V328G, V328H, V328I, V328K, V328L, V328M, V328N, V328P, V328Q, V328R, V328S, V328T, V328W, and V328Y.

Preferably, the amino acid sequence is engineered compared to SEQ ID NO:5 in at least one position such that it comprises a substitution selected from the group consisting of V328A, V328C, V328G, V328P, V328S, and V328T.

Preferably, the amino acid sequence is engineered compared to SEQ ID NO:5 in at least one position such that it comprises the substitution V328G.

In preferred embodiments, the amino acid sequence is additionally engineered compared to SEQ ID NO:5 in at least one further position selected from the group consisting of D48, Y60, Y164, P195, A242, A245, T409, K424, and V436.

In preferred embodiments, the amino acid sequence is additionally engineered compared to SEQ ID NO:5 in at least one further positions by an amino acid residue selected from the group consisting of V13, E15, M22, P35, T39, T50, R51, N57, L59, A73, A74, E77, L79, T88, V93, V115, T120, L140, H146, D147, Y148, W151, L161, E237, G243, S244, V271, L272, S302, K314, K358, E362, Y363, H375, L387, H410, G434, M437, T440, R442, and S450.

In preferred embodiments, the amino acid sequence is additionally engineered compared to SEQ ID NO:5 in at least one further position such that it comprises a substitution selected from the group consisting of V13L, E15R, M22F, M22C, M22V, M22L, M22A, M22W, P35L, P35I, T39Y, D48G, T50R, T50N, T50H, R51K, N57S, L59F, L59W, L59V, L59A, L59S, L59G, Y60A, Y60I, Y60L, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161F, L161M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, 5302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

Preferably, the amino acid sequence is engineered compared to SEQ ID NO:5 in
(i) at least one position such that it comprises the substitutions N268A; or V328G; or F25L; and
(ii) at least one further position selected from the group consisting of V13, E15, M22, P35, T39, D48, T50, R51, N57, L59, Y60, A73, A74, E77, L79, T88, V93, V115, T120, L140, H146, D147, Y148, W151, L161, Y164, P195, E237, A242, G243, S244, A245, V271, L272, S302, K314, K358, E362, Y363, H375, L387, T409, H410, K424, G434, V436, M437, T440, R442, and S450.

Preferably, the amino acid sequence is engineered compared to SEQ ID NO:5 in
(i) at least one position such that it comprises the substitutions N268A; or V328G; or F25L; and
(ii) at least one further position such that it comprises a further substitution selected from the group consisting of V13L, E15R, M22F, M22C, M22V, M22L, M22A, M22W, P35L, P35I, T39Y, D48G, T50R, T50N, T50H, R51K, N57S, L59F, L59W, L59V, L59A, L59S, L59G, Y60A, Y60I, Y60L, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161F, L161M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, S302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

Preferably, the homology of the amino acid sequence to SEQ ID NO:1 is at least 85%, more preferably at least 90%, still more preferably at least 95%, and most preferably at least 97%.

In a preferred embodiment, the homology of the amino acid sequence to SEQ ID NO:2 is at least 95%, more preferably at least 97%, and most preferably at least 99%.

In another preferred embodiment, the homology of the amino acid sequence to SEQ ID NO:3 is at least 95%, more preferably at least 97%, and most preferably at least 99%.

In still another preferred embodiment, the homology of the amino acid sequence to SEQ ID NO:4 is at least 95%, more preferably at least 97%, and most preferably at least 99%.

In still another preferred embodiment, the homology of the amino acid sequence to SEQ ID NO:5 is at least 95%, more preferably at least 97%, and most preferably at least 99%.

Preferably, the transaminase comprises an amino acid sequence of SEQ ID NO:2, SEQ ID NO:3, SEQ ID NO:4, or SEQ ID NO:5.

Preferably, the ATA according to the invention is capable of catalyzing the conversion of a ketone substrate (A) to an amine (C). Concomitantly, the ATA according to the invention is capable to catalyzing the conversion of an amine donor molecule (B) to a ketone product (D). Also preferably, the ATA according to the invention is capable of catalyzing the conversion of an amine (C) to a ketone product (A), thereby concomitantly catalyzing the conversion of an amine acceptor (D) into an amine molecule (B):

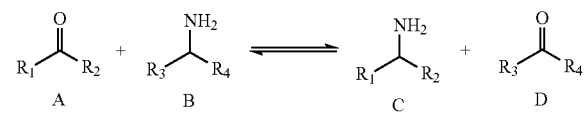

In a preferred embodiment, the ATA according to the invention is capable of catalyzing the stereoselective conversion of a ketone substrate (A) to a chiral (S)-amine (C), and/or vice versa of a chiral (S)-amine (C) to a ketone product (A).

In another preferred embodiment, the ATA according to the invention is capable of catalyzing the stereoselective conversion of a ketone substrate (A) to a chiral (R)-amine (C), and/or vice versa of a chiral (R)-amine (C) to a ketone product (A).

Preferably, the transaminase according to the invention is capable of catalyzing the conversion of (i) a ketone substrate according to general formula (I)

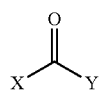

to an amine product according to general formula (II)

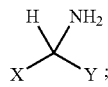

and/or the preferably concomitant conversion of
(ii) an amine cosubstrate according to general formula (III)

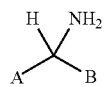

to a ketone coproduct according to general formula (IV)

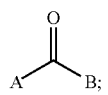

or vice versa;
wherein the amine product according to general formula (II) preferably has (S)-configuration or (R)-configuration at the central carbon atom as shown in general formula (II); and wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —S(=O)$_{1-2}$OH, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2$H, CO—$C_{1-2}$-alkyl, —CO—$C_{6-10}$-aryl and —CO-heteroaryl.

A skilled person recognizes that when X≠Y≠hydrogen, the central carbon atom as shown in general formula (II) is chiral and may have either (S)-configuration or (R)-configuration. The same applies to A, B and general formula (IV).
Preferably, the ATA according to the invention is preferably capable of catalyzing the stereoselective conversion of
(i) a ketone substrate according to general formula (I)

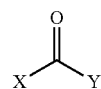

to a chiral amine product according to general formula (II)

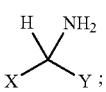

and/or the preferably concomitant conversion of
(ii) a chiral or non-chiral amine cosubstrate according to general formula (III)

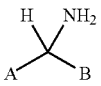

to a ketone coproduct according to general formula (IV)

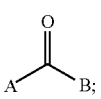

or vice versa;
wherein the chiral amine product according to general formula (II) preferably has (S)-configuration or (R)-configuration; and
wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO— heteroaryl, —SH, —SC$_{1-12}$-alkyl, —SC$_{6-10}$-aryl, —S-heteroaryl, —S(═O)$_{1-2}$OH, —NO, —NO$_2$, —N$_3$, —NH$_2$, —NH(C$_{1-12}$-alkyl), —N(C$_{1-12}$-alkyl)$_2$, —NH (C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl.

X and Y as well as A and B, in either case, independently of one another, can be alkyl, cycloalkyl, alkylcycloalkyl, aryl, alkylaryl, heteroaryl or alkylheteroaryl, which in each case can be unsubstituted or substituted with one or more chemical groups that do not interfere with enzyme catalysis, and where X or Y as well as A and B may be hydrogen. Further, X and Y may not be identical in structure and chirality, and may already contain a center of chirality. X and Y may also form a ring, which may be substituted or unsubstituted or fused to other rings. A and B of the cosubstrate may be identical or not identical in structure or chirality, and like X and Y, may form a ring, which may be substituted or unsubstituted or fused to other rings.

Preferably, X and Y as well as A and B, in either case, independently of one another, are each independently selected from unsubstituted or mono- or polysubstituted C$_{1-12}$-alkyl; unsubstituted or mono- or polysubstituted C$_{6-10}$-aryl, optionally being bridged through a unsubstituted or mono- or polysubstituted C$_{1-12}$-alkylene residue; unsubstituted or mono- or polysubstituted heteroaryl, optionally being bridged through a unsubstituted or mono- or polysubstituted aliphatic C$_{1-12}$-alkylene residue; and sugar residues or desoxysugar residues in each case comprising mono-, di- or oligosaccharides;

wherein mono- or polysubstituted means independently substituted with one or more functional groups selected from -halo, —OH, ═O, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(═O)$_{1-2}$OH, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl.

For the purpose of the description, saturated or unsaturated aliphatic C$_{1-12}$-hydrocarbon residues include but are not limited to alkyl, alkenyl and alkynyl residues, such as —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH═CH$_2$, —CH═CHCH═CH$_2$, —C≡CH, and —CH═CHC≡CH.

For the purpose of the description, saturated or unsaturated alicyclic C$_{1-12}$-hydrocarbon residues include but are not limited to C$_{3-12}$-cycloalkyl, wherein 1 or 2 carbon ring atoms may optionally be replaced by heteroatoms selected from N, O and S (C$_{1-12}$-heterocycloalkyl).

For the purpose of the description, C$_{6-10}$-aromatic hydrocarbon residues (═C$_{6-10}$-aryl) include but are not limited to phenyl and naphthyl.

For the purpose of the description, heteroaromatic hydrocarbon residues (=heteroaryl) include but are not limited to monocyclic ring systems, bicyclic ring systems and tricyclic ring systems. Examples of monocyclic heteroaryls include but are not limited to azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Examples of bicyclic heteroaryls include but are not limited to benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Examples of tricyclic heteroaryls include but are not limited to acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

For the purpose of the description, mono- or polysubstituted with regard to alkyl (e.g. —C$_{1-12}$-alkyl), cycloalkyl (e.g. —C$_{3-8}$-cycloalkyl), aryl (e.g. —C$_{6-10}$-aryl) and heteroaryl, respectively, preferably independently means replacement of a hydrogen from the core by one or more functional groups selected from -halo (preferably —F, —Cl, —Br, —I), —OH, ═O, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(═O)$_{1-2}$OH, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl.

For the purpose of the description, sugar residues or desoxysugar residues in each case comprising mono-, di- or oligosaccharides means that the ketone substrate of general formula (I) or the amine cosubstrate of general formula (III) may be a polyhydroxycarbonyl compound, optionally linked to other polyhydroxycarbonyl compounds through acetal and/or ketal bonds. For example, when X is C$_1$ alkyl monosubstituted with —OH and Y is C$_2$ alkyl polysubstituted with —OH, wherein every carbon atom bears a single —OH substituent, the ketone substrate of general formula (I) is a ketotetrose encompassing both enantiomers, D-erythrulose as well as L-erythrolose. Analogously, the ketone substrate of general formula (I) may be a ketopentose or a ketohexose which in turn may be linked to other sugar residues thus forming disaccharides or oligosaccharides.

Preferably, the ATA according to the invention is capable converting a ketone substrate to an amine with a broad specific activity for amine donor substrates chosen. Suitable amine donors may be selected according their specific activity in a given reaction. Examples for amine donors that can be used with the invention include, without limitation, isopropylamine (hereinafter also referred to as "IPA", also known as 2-aminopropane or propan-2-amine), phenylethylamine (also known as 1-phenylethylamine, and often also incorrectly referred to as methyl-benzylamine, hereinafter also referred to as "MBA"), 1-methyl-3-phenylpropylamine (also known as 2-amino-4-phenylbutane), glycine, glutamic acid, glutamate, monosodium glutamate, D-alanine, L-alanin, aspartic acid, lysine, ornithine, β-alanine, taurine, n-octylamine, cyclohexylamine, 1,4-butanediamine, 1,6-hexanediamine, 6-aminohexanoic acid, 4-ammobutyric acid, tyramine, and benzyl amine, 2-aminobutane, 2-amino-1-butanol, 1-amino-1-phenylethane, 1-amino-1-(2-methoxy- 5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane (also known as norfenfluramine), 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, each example also including its structure enantiomers and isomers, as the case may be and where possible, and including all possible salts thereof.

Preferably, the ATA according to the invention is capable converting an amine to a ketone substrate with a broad specific activity for amine acceptor substrates chosen. Suitable amine acceptors may be selected according their specific activity in a given reaction. Examples for amine acceptors that can be used with the invention include, without limitation, 1-phenylethanone (also known as acetophenone, hereinafter referred to as "AP"), 4-phenyl-2-butanone (also known as benzylacetone, hereinafter referred to as "BA"), 2-oxo-acetic acid, 2-oxo-pentanedioic acid (also known as alpha-ketoglutaric acid), 5-amino-2-oxo-pentanoic acid, pyruvate, 2-ketosuccinic acid, 6-amino-2-oxo-hexanoic acid, 6-oxo-norleucine, 5-amino-2-oxo pentanoic acid, 5-oxo-norvaline, 3-oxo-propanoic acid, 2-oxo-ethanesulfonic acid, octanal, cyclohexanone, 4-aminobutanal, butanedial, 6-amino-hexanal, hexanedial, 6-oxo-hexanoic acid, 4-oxo-butyric acid, 4-hydroxy-benzeneacetaldehyde, benzaldehyde, 2-butanone, 1-hydroxy-2-butanone, 1-phenylethanone, 1-(5-fluoro-2-methoxyphenyl)-ethanone, 1-phenyl-1-propanone, 1-(4-hydroxyphenyl)-1-propanone, 1-phenyl-1-propanone, 1-(4-bromophenyl)-1-propanone, 1-phenyl-1-propanone, 1-(4-nitrophenyl)-1-propanone1-phenyl-2-propanone, 1-(3-trifluoromethylphenyl)-2-propanone, 1-Hydroxy-2-propanone, 1-phenyl-1-butanone, 1-phenyl-2-butanone, 1-(2.5-dimethoxy-4-methylphenyl)-2-butanone, 1-phenyl-3-butanone, 1-(4-hydroxyphenyl)-3-butanone, 2-methyl-cyclopentanone, 3-methylcyclopentanone, 2-methylcyclohexanone, 1-(2-naphthalenyl)ethanone, 1-methyl-3-cyclopentanone, 2-methylcyclopentanone, 2-ethylcyclopentanone, 2-methylcyclohexanone, 3-methylcyclohexanone, 1,2,3,4-tetrahydro-1-oxonaphthalene, 1,2,3,4-tetrahydro-2-naphthalenone, 2-oxo-5-methoxy-1,2,3,4-tetrahydronaphthalene and 1-indone, each example including its structure enantiomers and isomers, as the case may be and where possible, and including all possible salts thereof.

Preferably, the transaminase according to the invention is characterized by either (A) a temperature stability of at least 50° C., preferably 55° C., and most preferably of 60° C., and/or (B) a specific activity of at least 0.05 U/mg, 0.06 U/mg, 0.07 U/mg, 0.08 U/mg, 0.09 U/mg, 0.1 U/mg, 0.15 U/mg, 0.2 U/mg, 0.25 U/mg, 0.3 U/mg, 0.35 U/mg, 0.4 U/mg, 0.45 U/mg, 0.5 U/mg, preferably, 0.75 U/mg, more preferably of 1 U/mg, and most preferably of 1.1 U/mg in Transaminase Standard Assays; and/or (C) a high conversion activity under different reaction conditions involving high amine concentrations.

Preferably, the transaminase according to the invention is engineered compared to SEQ ID NO:1 in at least one or more positions such that (A) the stereoselectivity of the engineered transaminase is higher than that of the wildtype transaminase of SEQ ID NO:1; and/or (B) the thermostability of the engineered transaminase is higher than that of the wildtype transaminase of SEQ ID NO:1; and/or (C) the conversion of the engineered transaminase is higher than that of the wildtype transaminase of SEQ ID NO:1.

Preferably, the engineered ATA of SEQ ID NO:1 according to the invention comprises an amino acid sequence of at least 50% homology, preferably at least 55%. more preferably at least 60%, even more preferably at least 70%, still more preferably at least 80%, yet more preferably at least 90% homology, yet more preferably at least 91% homology, yet more preferably at least 92% homology, yet more preferably at least 93% homology, yet more preferably at least 94% homology, yet more preferably at least 95% homology, yet more preferably at least 96% homology, yet more preferably at least 97% homology, yet more preferably at least 98% homology, yet more preferably at least 99% homology, yet more preferably at least 99.1% homology, yet more preferably at least 99.2% homology, yet more preferably at least 99.3% homology, yet more preferably at least 99.4% homology, yet more preferably at least 99.5% homology, yet more preferably at least 99.6% homology, yet more preferably at least 99.7% homology, yet more preferably at least 99.8% homology, or at least 99.9%, homology to SEQ ID NO:1, SEQ ID NO:2, SEQ ID NO:3, SEQ ID NO:4, and/or SEQ ID NO:5.

In a specific embodiment of this invention, any engineered amino acid sequence of SEQ ID NO:1 in comparison to the non-engineered amino acid sequence of SEQ ID NO:1 provides an improved stereoselectivity of at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 98%, preferably at least 99%, preferably at least 99.5%, and most preferably at least 99.9%; and/or provides a thermostability of at least 65° C., more preferably at least 70° C., still more preferably at least 75° C., still more preferably at least 80° C., and most preferably at least 85° C.; and/or provides a further increased conversion of preferably at least 35%, preferably at least 40%, preferably at least 45%, preferably at least 50%, preferably at least 55%, preferably at least 60%, preferably at least 65%, preferably at least 70%, preferably at least 75%, preferably at least 802%, preferably at least 85%, preferably at least 90%, preferably at least 55%, preferably at least 95%, and most preferably of at least 99%; and/or provides an improved conversion and an increased substrate specificity for of substrate specificity and/or activity for (R)-phenylacetylcarbinol, 1-phenyl-1-butanone, 2-methyl-1-phenyl-1-propanone, 1-phenyl-1-pentanone, methyl-3-oxo-3-phenylpropanoate, and/or methyl 3-oxo-3-phenyl-butyrate.

Another aspect of the invention relates to a method for the conversion of (i) a ketone substrate according to general formula (I) as described above to an amine product according to general formula (II) as described above;

and/or the preferably concomitant conversion of
(ii) an amine cosubstrate according to general formula (III) as described above to a ketone coproduct according to general formula (IV) as described above,
or vice versa;
wherein the amine product according to general formula (II) preferably has (S)-configuration or (R)-configuration; and
wherein the method comprises the step of reacting a ketone substrate according to general formula (I) and/or an amine product according to general formula (II) and/or an amine cosubstrate according to general formula (III) and/or a ketone coproduct according to general formula (IV) in the presence of an ATA according to the invention.

Preferably, the invention relates to a method for the stereoselective conversion of
(i) a ketone substrate according to general formula (I) as described above to a chiral amine product according to general formula (II) as described above;
and/or the preferably concomitant conversion of
(ii) a chiral or non-chiral amine cosubstrate according to general formula (III) as described above to a ketone coproduct according to general formula (IV) as described above,
or vice versa;
wherein the chiral amine product according to general formula (II) preferably has (S)-configuration or (R)-configuration; and
wherein the method comprises the step of reacting a ketone substrate according to general formula (I) and/or a chiral amine product according to general formula (II) and/or a chiral or non-chiral amine cosubstrate according to general formula (III) and/or a ketone coproduct according to general formula (IV) in the presence of an ATA according to the invention.

Preferably, the method according to the invention is for the conversion of
(i) a ketone substrate according to general formula (I)

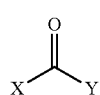

(I)

to an amine product according to general formula (II)

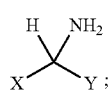

(II)

and/or the preferably concomitant conversion of
(ii) a cosubstrate according to general formula (III)

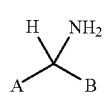

(III)

to a ketone coproduct according to general formula (IV)

(IV)

or vice versa;
wherein X and Y as well as A and B, in either case, independently of one another, are selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein one of residues X or Y, as well as one of residues A or B, in either case, independently of one another, may be hydrogen;
wherein mono- or polysubstituted means independently substituted with one or more functional groups selected from -halo, —OH, =O, —O$C_{1-12}$-alkyl, —O$C_{6-10}$-aryl, —O-heteroaryl, —OCO$C_{1-12}$-alkyl, —OCO$C_{6-10}$-aryl, —OCO— heteroaryl, —SH, —S$C_{1-12}$-alkyl, —S$C_{6-10}$-aryl, —S-heteroaryl, —S(=O)$_{1-2}$OH, —NO, —NO$_2$, —N$_3$, —NH$_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —CO$_2$H, CO—$C_{1-2}$-alkyl, —CO—$C_{6-10}$-aryl and —CO-heteroaryl;
wherein the method comprises the step of reacting a ketone substrate according to general formula (I) and/or an amine product according to general formula (II) and/or a amine cosubstrate according to general formula (III) and/or a ketone coproduct according to general formula (IV) in the presence of a transaminase as claimed.

Another aspect of the invention relates to the use of an ATA according to the invention as described above for the amidation of a keto group in any possible direction, preferably in the method according to the invention as described above.

Preferably, the invention relates to the use of an ATA according to the invention as described above for the conversion of
(i) a ketone substrate according to general formula (I) as described above to an amine product according to general formula (II) as described above;
and/or the preferably concomitant conversion of
(ii) an amine cosubstrate according to general formula (III) as described above to a ketone coproduct according to general formula (IV) as described above,
or vice versa;
wherein the amine product according to general formula (II) preferably has (S)-configuration or (R)-configuration.

Preferably, the invention relates to the use of an ATA according to the invention as described above for the stereoselective conversion of
(i) a ketone substrate according to general formula (I) as described above to a chiral amine product according to general formula (II) as described above;

and/or the preferably concomitant conversion of
(ii) a chiral or non-chiral amine cosubstrate according to general formula (III) as described above to a ketone coproduct according to general formula (IV) as described above,
or vice versa;
wherein the chiral amine product according to general formula (II) has (S)-configuration or (R)-configuration.

The following examples further illustrate the invention but are not to be construed as limiting its scope.

The amino acid sequence of SEQ ID NO:2 was systematically substituted in positions F25, A268, V328, and L255. In each case, only a single position was substituted compared to SEQ ID NO:2. The following thus obtained mutants of SEQ ID NO:2 have the following SEQ ID NOS in the sequence listing:

| | |
|---|---|
| SEQ ID NO: 6 | F25D |
| SEQ ID NO: 7 | F25E |
| SEQ ID NO: 8 | F25H |
| SEQ ID NO: 9 | F25K |
| SEQ ID NO: 10 | F25R |
| SEQ ID NO: 11 | F25N |
| SEQ ID NO: 12 | F25Q |
| SEQ ID NO: 13 | F25S |
| SEQ ID NO: 14 | F25T |
| SEQ ID NO: 15 | F25C |
| SEQ ID NO: 16 | F25G |
| SEQ ID NO: 17 | F25P |
| SEQ ID NO: 18 | F25A |
| SEQ ID NO: 19 | F25I |
| SEQ ID NO: 20 | F25L |
| SEQ ID NO: 21 | F25M |
| SEQ ID NO: 22 | F25V |
| SEQ ID NO: 23 | F25W |
| SEQ ID NO: 24 | F25Y |
| SEQ ID NO: 25 | A268D |
| SEQ ID NO: 26 | A268E |
| SEQ ID NO: 27 | A268H |
| SEQ ID NO: 28 | A268K |
| SEQ ID NO: 29 | A268R |
| SEQ ID NO: 30 | A268N |
| SEQ ID NO: 31 | A268Q |
| SEQ ID NO: 32 | A268S |
| SEQ ID NO: 33 | A268T |
| SEQ ID NO: 34 | A268C |
| SEQ ID NO: 35 | A268G |
| SEQ ID NO: 36 | A268P |
| SEQ ID NO: 37 | A268F |
| SEQ ID NO: 38 | A268I |
| SEQ ID NO: 39 | A268L |
| SEQ ID NO: 40 | A268M |
| SEQ ID NO: 41 | A268V |
| SEQ ID NO: 42 | A268W |
| SEQ ID NO: 43 | A268Y |
| SEQ ID NO: 44 | V328D |
| SEQ ID NO: 45 | V328E |
| SEQ ID NO: 46 | V328H |
| SEQ ID NO: 47 | V328K |
| SEQ ID NO: 48 | V328R |
| SEQ ID NO: 49 | V328N |
| SEQ ID NO: 50 | V328Q |
| SEQ ID NO: 51 | V328S |
| SEQ ID NO: 52 | V328T |
| SEQ ID NO: 53 | V328C |
| SEQ ID NO: 54 | V328G |
| SEQ ID NO: 55 | V328P |
| SEQ ID NO: 56 | V328A |
| SEQ ID NO: 57 | V328F |
| SEQ ID NO: 58 | V328I |
| SEQ ID NO: 59 | V328L |
| SEQ ID NO: 60 | V328M |
| SEQ ID NO: 61 | V328W |
| SEQ ID NO: 62 | V328Y |
| SEQ ID NO: 63 | L255D |
| SEQ ID NO: 64 | L255E |
| SEQ ID NO: 65 | L255H |
| SEQ ID NO: 66 | L255K |
| SEQ ID NO: 67 | L255R |
| SEQ ID NO: 68 | L255N |
| SEQ ID NO: 69 | L255Q |
| SEQ ID NO: 70 | L255S |
| SEQ ID NO: 71 | L255T |
| SEQ ID NO: 72 | L255C |
| SEQ ID NO: 73 | L255G |
| SEQ ID NO: 74 | L255P |
| SEQ ID NO: 75 | L255A |
| SEQ ID NO: 76 | L255F |
| SEQ ID NO: 77 | L255I |
| SEQ ID NO: 78 | L255M |
| SEQ ID NO: 79 | L255V |
| SEQ ID NO: 80 | L255W |
| SEQ ID NO: 81 | L255Y |

EXAMPLE 1: CHARACTERIZATION OF ENZYMATIC PROPERTIES OF ENGINEERED ATA OF SEQ ID NO:2 AND SEQ ID NO:5

The gene sequences coding for the ATA corresponding to SEQ ID NO:2 and SEQ ID NO:5 were cloned into the expression vector pLE1A17 (derivative of pRSF-1b, Novagen). The resulting plasmids were used for transformation of E. coli BL21(DE3) cells.

For expression of the ATA corresponding to SEQ ID NO:2 and SEQ. ID NO:5 cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.1 mM) and carried out at 30° C. for 16-18 hours.

Cells were harvested by centrifugation (3220×g, 20 min, 4° C.) and disrupted by resuspending corresponding to an optical density, measured at 600 nm (0D600) of 100 with cell lysis buffer (50 mM Tris-HCl pH 7.0; 2 mM MgCl2, 1× CelLytic B (Sigma); DNA nuclease 0.02 U, lysozyme 0.5 mg/ml). The crude extracts were separated from cell debris by centrifugation (3220×g 30 min, 4° C.), resulting in enzymatic active preparations of the ATA of SEQ ID NO:2 and SEQ ID NO:5, respectively. For detection of the enzymatic activity of an ATA of the invention, a lyophilisate of the active preparation of the ATA may be obtained. The crude extract or lyophilisate was investigated regarding the ATA activity using the Transaminase Standard Assay.

The Transaminase Standard Assay monitors the conversion of racemic 1-phenylethan-1-amine (MBA) and pyruvate to 1-phenylethanone (Acetophenone) and L-alanine. The reaction is performed at 30° C. in 50 mM phosphate buffer (pH 7, 4) and 0.1 mM pyridoxalphosphate (PLP) using 10 mM racemic 1-phenylethan-1-amine and 10 mM sodium-pyruvate as substrates. The production of 1-phenylehanone is followed photometrically at 300 nm. One unit (U) liberates 1 µmol 1-phenylethanone (Acetophenone) per minute. Specific activity refers to units per milligram crude extract lyophilisate (U/mg)

Furthermore, the thermostability of each enzyme was analyzed. For this purpose, melting profiles of these active enzymatic active preparations of a respective ATA were recorded by incubation the crude extract for 15 minutes at different temperatures in a PCR cycler. Afterwards the crude extracts were incubated on ice for 30 minutes. Insoluble proteins were separated by centrifugation and the supernatants were analyzed regarding their remaining ATA activity in a Transaminase Standard Assay as described above.

Thermostability was expressed as the temperature at which 80% of the initial activity of the ATA variant remains after 15 min of incubation [Tm(80%)]. The initial activity is the activity of the respective ATA variant without any high temperature treatment, i.e. with 15 min incubation on ice instead of incubation at different temperatures in a PCR cycler.

| seq reference | Tm(80%) [° C.] | Activity (Transaminase Standard Assay) [U/mg] |
|---|---|---|
| SEQ ID NO: 5 | 57 | 0.2 |
| SEQ ID NO: 2 | 59 | 0.1 |

Additionally the conversion properties of these enzymes were investigated in Transaminase Conversion Assays.

Transaminase Conversion Assays monitor enzyme properties at different reaction conditions that are relevant for a preparative synthesis application at high concentration of different amine donors, isopropylamine (IPA), racemic 1-phenylethan-1-amine (MBA) or (S)-1-phenylethan-1-amine (S-MBA) or racemic alanine, respectively. The ketone acceptor was 4-phenyl-2-butanone (BA). The reaction was performed at 30° C. in 50 mM phosphate buffer (pH 7, 4) and 0.1 mM pyridoxalphosphate (PLP).

Conversion from BA to 1-methyl-3-phenylpropylamine was analyzed by HPLC after a given time of reaction, typically 6 h or 20 h. Analytical conditions are:

Column: Gemini 5μ C18, 150×4.6 mm (Phenomenex);
Eluents: A) dH2O, 0.1% trifluoroacetic acid (TFA); B) Acetonitrile, 0.1% TFA;
Flow: 1 ml/min; gradient: 20% B to 80% B in 6 min, hold for 1 min, to 20% B in 1 min, hold for 3 min;
Oven temperature: 35° C.;
Detection: 210 nm.

The retention times of the analytes are 6.52 min for BA and 3.65 min for 1-methyl-3-phenylpropylamine.

Overall, Transaminase Conversion Assays may be done at conditions differing in the type of amine donor (IPA, MBA, and alanine) and the respective concentration of the reactants.

Condition A: 50 mM BA, 100 mM IPA; after 6 h
Condition B: 50 mM BA, 200 mM rac. MBA; after 6 h
Condition C: 50 mM BA, 500 mM IPA; after 6 h
Condition D: 50 mM BA, 1000 mM rac. MBA; after 6 h
Condition E: 50 mM BA, 200 mM rac. alanine; after 6 h
Condition K: 100 mM BA; 500 mM rac. MBA,
Condition L: 200 mM BA; 500 mM rac. MBA,
Condition M: 10 g/L BA, 900 mM IPA.

Active enzyme preparations of SEQ ID NO:2 and SEQ ID NO:5 under this example were analyzed at the Conditions A, B, C, D, E, K, L, and M.

The characteristics of the active enzyme preparations of SEQ ID NO:2 and SEQ ID NO:5 are summarized in the Tables below.

| transaminase origin | % conversion cond. A | % conversion cond. B | % conversion cond. C | % conversion cond. D | % conversion cond. E |
|---|---|---|---|---|---|
| SEQ ID NO: 5 | 15.9 | 8.2 | 27.0 | 0.0 | 1.6 |
| SEQ ID NO: 2 | 33.7 | 88.8 | 70.7 | 54.8 | 1.6 |

| transaminase origin | % conversion cond. K | % conversion cond. L | % conversion cond. M | Tm(80%) [° C.] | ee % |
|---|---|---|---|---|---|
| SEQ ID NO: 5 | 0.0 | 0.0 | 0.0 | 57 | |
| SEQ ID NO: 2 | 74 | 53 | 80 | 58 | >99 |

EXAMPLE 2: GENERATION AND EXPRESSION OF ATA SEQ ID NO:2 MUTANT LIBRARIES

Mutant libraries of SEQ ID NO:2 were generated for positions 25, 255, 268, and 328, using standard protocols for site saturation mutagenesis, generating the full set of variants exhibiting each one of all 20 canonical amino acids for a given position. Genes were cloned into the expression vector pLE1A17 (derivative of pRSF-1b, Novagen). The resulting plasmids were used for transformation of E. coli BL21(DE3) cells.

For expression of the new ATA variants corresponding to SEQ IDs NO:6-SEQ IDs NO:81, cells were cultivated in ZYM505 medium (F. William Studier, Protein Expression and Purification 41 (2005) 207-234) supplemented with kanamycin (50 mg/l) at 37° C. Expression of the genes was induced at logarithmic phase by IPTG (0.1 mM) and caned out at 30° C. for 16-18 hours.

Cells were harvested by centrifugation (3220×g, 20 min, 4° C.) and disrupted by resuspending corresponding to an optical density, measured at 600 nm (OD600) of 100 with cell lysis buffer (50 mM Tris-HCl pH 7.0; 2 mM MgCl2, 0.1 mM pyridoxalphosphate (PLP), 1× CelLytic B (Sigma); DNA nuclease 0.02 U, lysozyme 0.5 mg/mL). The crude extracts were separated from cell debris by centrifugation (3220×g 30 min, 4° C.), resulting in enzymatic active preparations of the ATA variants of SEQ IDs NO:6-SEQ IDs NO:81.

The crude extract or crude extract with additional heat treatment was investigated regarding the ATA activity using the Transaminase Standard Assay as described in Example 1.

EXAMPLE 3: CHARACTERIZATION OF RELATIVE TRANSAMINASE ACTIVITY OF SITE-SATURATION VARIANTS DERIVED FROM SEQ ID NO:2

Active enzyme preparations (crude extracts) of engineered ATA-variants SEQ IDs NO:6-SEQ IDs NO:81 from site-saturation libraries, obtained as described in Example 2, were characterized using the Transaminase Standard Assay as described above, at a final dilution suitable for detection of linear slopes. Activity data are indicated as relative activity, describing the activity (slope fitted as initial rates to linear parts of time-courses) of a given mutant variant in relation to the activity of SEQ ID NO:2, which was determined in parallel during the same experiment.

The experimental results are summarized in the below table.

EXAMPLE 4: COMPARATIVE STUDY OF THE EFFECT OF THERMAL INCUBATION ON CRUDE LYSATES OF SITE-SATURATION VARIANTS OF SEQ ID NO:2

Active enzyme preparation (crude extracts) of engineered ATA-variants SEQ IDs NO:6-SEQ IDs NO:81 from site-saturation libraries, obtained as described in Example 2, were characterized for their relative activities after heat-treatment at 66° C. Crude extracts were incubated at 66° C. for 15 min, subsequently incubated on ice for 30 min. Aggregated proteins were sedimented by centrifugation (3220×g, 20 min, 4° C.).

Relative activities of crude extracts following this treatment were determined using the Transaminase Standard Assay as described in Examples 1, at a final dilution suitable for detection of linear slopes. Activity data are indicated as relative activity after heat-incubation, describing the activity after heat-incubation (slope fitted as initial rates to linear parts of time-courses) of a given mutant in relation to the activity after heat-incubation of SEQ ID NO:2, which was determined in parallel during the same experiment.

The experimental results are summarized in the below table.

|  | single substitution compared to SEQ ID NO: 2 | relative activity at 30° C. according to Example 3 | relative activity at 30° C., after heat-incubation at 66° C. according to Example 4 |
| --- | --- | --- | --- |
| SEQ ID NO: 6 | F25D | 0.13 | 0.12 |
| SEQ ID NO: 7 | F25E | 0.05 | 0.10 |
| SEQ ID NO: 8 | F25H | 1.37 | 0.14 |
| SEQ ID NO: 9 | F25K | 0.03 | 0.14 |
| SEQ ID NO: 10 | F25R | 1.48 | 0.20 |
| SEQ ID NO: 11 | F25N | 1.90 | 0.13 |
| SEQ ID NO: 12 | F25Q | 2.01 | 0.16 |
| SEQ ID NO: 13 | F25S | 2.09 | 0.12 |
| SEQ ID NO: 14 | F25T | 1.68 | 0.10 |
| SEQ ID NO: 15 | F25C | 2.10 | 0.10 |
| SEQ ID NO: 16 | F25G | 2.93 | 0.12 |
| SEQ ID NO: 17 | F25P | 0.11 | 0.12 |
| SEQ ID NO: 18 | F25A | 1.74 | 0.15 |
| SEQ ID NO: 2 | — | 1.00 | 1.00 |
| SEQ ID NO: 19 | F25I | 1.26 | 0.14 |
| SEQ ID NO: 20 | F25L | 1.41 | 0.65 |
| SEQ ID NO: 21 | F25M | 1.81 | 0.17 |
| SEQ ID NO: 22 | F25V | 1.35 | 0.12 |
| SEQ ID NO: 23 | F25W | 1.12 | 0.50 |
| SEQ ID NO: 24 | F25Y | 1.02 | 0.15 |
| SEQ ID NO: 25 | A268D | 0.30 | 0.30 |
| SEQ ID NO: 26 | A268E | 0.05 | 0.14 |
| SEQ ID NO: 27 | A268H | 0.54 | 0.14 |
| SEQ ID NO: 28 | A268K | 0.03 | 0.18 |
| SEQ ID NO: 29 | A268R | not detectable | 0.12 |
| SEQ ID NO: 30 | A268N | 0.13 | 0.46 |
| SEQ ID NO: 31 | A268Q | 0.25 | 0.39 |
| SEQ ID NO: 32 | A268S | 0.43 | 0.38 |
| SEQ ID NO: 33 | A268T | 0.32 | 0.18 |
| SEQ ID NO: 34 | A268C | 0.29 | 0.59 |
| SEQ ID NO: 35 | A268G | 0.08 | 0.12 |
| SEQ ID NO: 36 | A268P | 0.16 | 0.13 |
| SEQ ID NO: 2 | — | 1.00 | 1.00 |
| SEQ ID NO: 37 | A268F | 0.69 | 0.16 |
| SEQ ID NO: 38 | A268I | 0.68 | 0.24 |
| SEQ ID NO: 39 | A268L | 0.00 | 0.13 |
| SEQ ID NO: 40 | A268M | 0.09 | 0.07 |
| SEQ ID NO: 41 | A268V | 0.72 | 0.88 |
| SEQ ID NO: 42 | A268W | not detectable | 0.12 |
| SEQ ID NO: 43 | A268Y | 0.06 | 0.09 |
| SEQ ID NO: 44 | V328D | 0.25 | 0.11 |
| SEQ ID NO: 45 | V328E | 0.17 | 0.13 |
| SEQ ID NO: 46 | V328H | 0.18 | 0.17 |
| SEQ ID NO: 47 | V328K | 0.10 | 0.16 |
| SEQ ID NO: 48 | V328R | 0.11 | 0.21 |
| SEQ ID NO: 49 | V328N | 0.32 | 0.15 |
| SEQ ID NO: 50 | V328Q | 0.07 | 0.15 |
| SEQ ID NO: 51 | V328S | 1.22 | 0.12 |
| SEQ ID NO: 52 | V328T | 1.49 | 0.20 |
| SEQ ID NO: 53 | V328C | 1.57 | 0.16 |
| SEQ ID NO: 54 | V328G | 0.41 | 0.18 |
| SEQ ID NO: 55 | V328P | 1.47 | 0.09 |
| SEQ ID NO: 56 | V328A | 1.48 | 0.13 |
| SEQ ID NO: 57 | V328F | 0.24 | 0.14 |
| SEQ ID NO: 58 | V328I | 0.20 | 0.41 |
| SEQ ID NO: 59 | V328L | 0.01 | 0.16 |
| SEQ ID NO: 60 | V328M | 0.11 | 0.11 |
| SEQ ID NO: 2 | — | 1.00 | 1.00 |
| SEQ ID NO: 61 | V328W | 0.13 | 0.18 |
| SEQ ID NO: 62 | V328Y | 0.02 | 0.19 |
| SEQ ID NO: 63 | L255D | 0.16 | 0.11 |
| SEQ ID NO: 64 | L255E | 0.04 | 0.13 |
| SEQ ID NO: 65 | L255H | 0.33 | 0.11 |
| SEQ ID NO: 66 | L255K | 0.19 | 0.09 |
| SEQ ID NO: 67 | L255R | 0.18 | 0.12 |
| SEQ ID NO: 68 | L255N | 0.14 | 0.16 |
| SEQ ID NO: 69 | L255Q | 0.26 | 0.16 |
| SEQ ID NO: 70 | L255S | 0.12 | 0.17 |
| SEQ ID NO: 71 | L255T | 0.75 | 0.20 |
| SEQ ID NO: 72 | L255C | 0.10 | 0.09 |
| SEQ ID NO: 73 | L255G | 0.09 | 0.16 |
| SEQ ID NO: 74 | L255P | 0.11 | 0.13 |
| SEQ ID NO: 75 | L255A | 0.16 | 0.11 |
| SEQ ID NO: 76 | L255F | 0.53 | 0.44 |
| SEQ ID NO: 77 | L255I | 0.88 | 0.16 |
| SEQ ID NO: 2 | — | 1.00 | 1.00 |
| SEQ ID NO: 78 | L255M | 0.06 | 0.13 |
| SEQ ID NO: 79 | L255V | 0.66 | 0.17 |
| SEQ ID NO: 80 | L255W | 0.25 | 0.08 |
| SEQ ID NO: 81 | L255Y | 0.26 | 0.11 |

The invention claimed is:

1. A transaminase comprising an amino acid sequence with at least 80% sequence identity to SEQ ID NO: 1, wherein the amino acid sequence is engineered compared to SEQ ID NO: 1 in at least two positions such that the transaminase comprises:
   (i) at position F255 a substitution to F255L; and
   (ii) at position N268 a substitution selected from the group consisting of N268A, N268D, N268F, N268H, N268I, N268K, N268L, N268M, N268P, N268Q, N268R, N268V, and N268W.

2. The transaminase according to claim 1, wherein the substitution at position N268 is a substitution to N268A.

3. The transaminase according to claim 1, which is additionally engineered compared to SEQ ID NO: 1 in at least one further position selected from the group consisting of D48, Y60, Y164, P195, A242, A245, T409, K424, and V436 or from the group consisting of V13, E15, M22, P35, T39, T50, R51, N57, L59, A73, A74, E77, L79, T88, V93, V115, T120, L140, H146, D147, Y148, W151, L161, E237, G243, S244, V271, L272, S302, K314, K358, E362, Y363, H375, L387, H410, G434, M437, T440, R442, and S450, or from the group consisting of V13L, E15R, M22F, M22C, M22V, M22L, M22A, M22W, P35L, P35I, T39Y, D48G, T5OR, T5ON, T5OH, R51 K, N57S, L59F, L59W, L59V, L59A, L59S, L59G, Y60A, Y60I, Y6OL, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151 I, W151F, W151Y, W151S, L161A, L161 F, L161 M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, S302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

4. The transaminase according to claim 3, which is engineered compared to SEQ ID NO: 1 in at least one further position such that it comprises a further substitution selected from the group consisting of V13L, E15R, M22F, M22C, M22V, M22L, M22A, M22W, P35L, P35I, T39Y, T5OR, T5ON, T5OH, R51 K, N57S, L59F, L59W, L59V, L59A, L59S, L59G, Y60A, Y60I, Y6OL, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161F, L161M, L161Y, L161I, L161Q, E237S, E237A, E237D, A242Y, A242G, G243A, G243I, S244A, S244G, S244I, S244L, V271A, L272I, L272A, S302G, K314E, K358E, E362R, Y363F, H375F, L387V, L387I, L387F, L387Y, L387T, L387A, L387C, H410K, H410E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

5. The transaminase according to claim 1, wherein the sequence identity of the amino acid sequence to SEQ ID NO: 1 is at least 90%.

6. The transaminase according to claim 1, wherein the amino acid sequence is engineered compared to SEQ ID NO: 1 in at least three positions, at least four positions, at least five positions, at least six positions, at least seven positions, at least eight positions, at least nine positions or at least ten positions.

7. A transaminase comprising an amino acid sequence according to SEQ ID NO: 2, SEQ ID NO: 3, or SEQ ID NO: 4.

8. The transaminase according to claim 1 providing at least one of the following:
   (A) a temperature stability of at least 50 ° C., preferably 55° C., and most preferably of 60° C.,
   (B) a specific activity of at least 0.5 U/mg, preferably, 0.75 U/mg, more preferably of 1 U/mg, and most preferably of 1.1 U/mg in Transaminase Standard Assays; or
   (C) a high conversion activity under different reaction conditions involving high amine concentrations.

9. The transaminase according to claim 1, which is engineered compared to SEQ ID NO: 1 in the at least two or more positions to result in an engineered transaminase and to provide at least one of the following:
   (A) stereoselectivity of the engineered transaminase is higher than that of the wildtype transaminase of SEQ ID NO: 1;
   (B) thermostability of the engineered transaminase is higher than that of the wildtype transaminase of SEQ ID NO: 1; or
   (C) conversion activity of the engineered transaminase is higher than that of the wildtype transaminase of SEQ ID NO: 1.

10. The transaminase according to claim 1, which is additionally engineered compared to SEQ ID NO: 1 in at least one further position selected from the group consisting of D48, Y60, Y164, P195, A242, A245, T409, K424, and V436 or
   from the group consisting of V13, E15, M22, P35, T39, T50, R51, N57, L59, A73, A74, E77, L79, T88, V93, V115, T120, L140, H146, D147, Y148, W151, L161, E237, G243, S244, V271, L272, S302, K314, K358, E362, Y363, H375, L387, H410, G434, M437, T440, R442, and S450, or
   from the group consisting of V13L, E15R, M22F, M22C, M22V, M22L, M22A, M22W, P35L, P35I, T39Y, D48G, T5OR, T5ON, T5OH, R51 K, N57S, L59F, L59W, L59V, L59A, L595, L59G, Y60A, Y60I, Y6OL, Y60F, Y60V, A73N, A74P, E77G, L79M, T88V, T88A, T88G, T88L, T88Y, V93T, V93N, V115I, T120S, L140K, H146Y, H146D, H146S, D147S, Y148F, Y148S, Y148G, W151A, W151I, W151F, W151Y, W151S, L161A, L161 F, L161 M, L161Y, L161I, L161Q, Y164F, Y164M, P195S, E237S, E237A, E237D, A242V, A242Y, A242G, G243A, G243I, S244A, S244G, S244I, S244L, A245T, V271A, L272I, L272A, S302G, K314E, K358E, E362R, Y363F, H375F, L387V, L387I, L387F, L387Y, L387T, L387A, L387C, T409R, H410K, H410E, K424E, G434A, G434V, G434L, G434Y, G434T, G434C, V436A, M437T, M437C, M437F, M437V, M437Y, M437A, T440H, T440S, T440N, R442V, R442S, R442A, R442L, R442C, and S450N.

11. The transaminase according to claim 5, wherein the sequence identity of the amino acid sequence to SEQ ID NO: 1 is at least 95%.

12. An engineered amino acid sequence comprising SEQ ID NO: 1, which has been substituted at at least two positions comprising: position F255 is substituted to F255L; position N268 is substituted to N268A, N268D, N268F, N268H, N268I, N268K, N268L, N268M, N268P, N268Q, N268R, N268V, or N268W.

13. The transaminase according to claim 7, wherein the amino acid sequence comprises SEQ ID NO: 2.

14. The transaminase according to claim 7, wherein the amino acid sequence comprises SEQ ID NO: 3.

15. The transaminase according to claim 7, wherein sequence identity of the amino acid sequence comprises SEQ ID NO: 4.

* * * * *

UNITED STATES PATENT AND TRADEMARK OFFICE
CERTIFICATE OF CORRECTION

PATENT NO. : 10,774,356 B2  
APPLICATION NO. : 15/735170  
DATED : September 15, 2020  
INVENTOR(S) : Andreas Vogel et al.

Page 1 of 1

It is certified that error appears in the above-identified patent and that said Letters Patent is hereby corrected as shown below:

In the Specification

In Column 11, Line 19, please delete "5244" and insert -- S244 --, therefore.

In Column 11, Line 26, please delete "5302" and insert -- S302 --, therefore.

In Column 11, Line 47, please delete "5450" and insert -- S450 --, therefore.

In Column 11, Line 52, please delete "5244," and insert -- S244, --, therefore.

In the Claims

In Column 241, Line 61, Claim 3, delete "T5OR, T5ON, T5OH, R51 K" and insert -- T50R, T50N, T50H, R51K --, therefore.

In Column 241, Line 62, in Claim 3, delete "Y6OL," and insert -- Y60L, --, therefore.

In Column 242, Lines 48-49, in Claim 4, delete "T5OR, T5ON, T5OH, R51 K" and insert -- T50R, T50N, T50H, R51K --, therefore.

In Column 242, Line 50, in Claim 4, delete "Y6OL," and insert -- Y60L, --, therefore.

In Column 244, Line 6, in Claim 10, delete "T5OR, T5ON, T5OH, R51 K" and insert -- T50R, T50N, T50H, R51K --, therefore.

In Column 244, Line 7, in Claim 10, delete "Y6OL," and insert -- Y60L, --, therefore.

In Column 244, Line 36, in Claim 15, delete "sequence" and insert -- the sequence --, therefore.

Signed and Sealed this  
Sixteenth Day of March, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 81

<210> SEQ ID NO 1
<211> LENGTH: 476
<212> TYPE: PRT
<213> ORGANISM: Arthrobacter citreus

<400> SEQUENCE: 1

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

-continued

```
Pro Val Pro Ile Glu Ser Thr Glu Gly Asp Tyr Leu Ile Met Pro Asp
             35                  40                  45

Gly Thr Arg Leu Leu Asp Phe Phe Asn Gln Leu Tyr Cys Val Asn Leu
 50                  55                  60

Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                 85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Tyr Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Phe Arg
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
```

```
                450             455             460
Leu Asp Tyr Leu Glu Ser Gly Glu Trp Gln Gln Ser
465                 470                 475

<210> SEQ ID NO 2
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 2

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335
```

```
Ala Met Ala Ala Val Cys Ala Asn Leu Glu Val Met Met Glu Asn
            340                 345                 350
Leu Val Glu Gln Ala Lys Asn Ser Gly Glu Tyr Ile Arg Ser Lys Leu
        355                 360                 365
Glu Leu Leu Gln Glu Lys His Lys Ser Ile Gly Asn Phe Asp Gly Tyr
    370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
            420                 425                 430
Ile Gly Gly Ala Met Pro Asn Thr Met Arg Ile Gly Ala Ser Leu Asn
        435                 440                 445
Val Ser Arg Gly Asp Ile Asp Lys Ala Met Asp Ala Leu Asp Tyr Ala
    450                 455                 460
Leu Asp Tyr Leu Glu Ser Gly Glu Trp Gln Gln Ser
465                 470                 475

<210> SEQ ID NO 3
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 3

Met Gly Leu Thr Val Gln Lys Ile Asn Trp Glu Gln Val Lys Glu Trp
1               5                   10                  15
Asp Arg Lys Tyr Leu Met Arg Thr Phe Ser Thr Gln Asn Glu Tyr Gln
                20                  25                  30
Pro Val Pro Ile Glu Ser Thr Glu Gly Asp Tyr Leu Ile Met Pro Asp
            35                  40                  45
Gly Thr Arg Leu Leu Asp Phe Phe Asn Gln Leu Tyr Cys Val Asn Leu
    50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
        115                 120                 125
Leu Asn Ile Ala Arg Leu Tyr Thr Asn Arg Pro Leu Val Val Thr Arg
    130                 135                 140
Glu His Asp Tyr His Gly Trp Thr Gly Gly Ala Ala Thr Val Thr Arg
145                 150                 155                 160
Leu Arg Ser Tyr Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Pro Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
    210                 215                 220
```

-continued

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Leu Arg
            245                 250                 255

Lys Met Thr Lys Glu Leu Gly Val Leu Trp Ile Asn Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Gly Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
            405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

```
<210> SEQ ID NO 4
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 4
```

Met Gly Leu Thr Val Gln Lys Ile Asn Trp Glu Gln Val Lys Glu Trp
1               5                   10                  15

Asp Arg Lys Tyr Leu Met Arg Thr Leu Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro

```
                100             105             110
Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Thr Arg
130                 135                 140

Glu His Asp Tyr His Gly Trp Thr Gly Gly Ala Ala Thr Val Thr Arg
145                 150                 155                 160

Leu Arg Ser Met Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Leu Arg
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 5
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 5

```
Met Gly Leu Thr Val Gln Lys Ile Asn Trp Glu Gln Val Lys Glu Trp
1               5                   10                  15
Asp Arg Lys Tyr Leu Met Arg Thr Phe Ser Thr Gln Asn Glu Tyr Gln
            20                  25                  30
Pro Val Pro Ile Glu Ser Thr Glu Gly Asp Tyr Leu Ile Met Pro Asp
        35                  40                  45
Gly Thr Arg Leu Leu Asp Phe Phe Asn Gln Leu Tyr Cys Val Asn Leu
    50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
        115                 120                 125
Leu Asn Ile Ala Arg Leu Tyr Thr Asn Arg Pro Leu Val Val Thr Arg
    130                 135                 140
Glu His Asp Tyr His Gly Trp Thr Gly Ala Ala Thr Val Thr Arg
145                 150                 155                 160
Leu Arg Ser Tyr Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Pro Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
    210                 215                 220
Asn Tyr Gly Pro Glu Gln Val Ala Ala Val Ile Thr Glu Val Ser Gln
225                 230                 235                 240
Gly Ala Gly Ser Ala Met Pro Pro Tyr Glu Tyr Ile Pro Gln Leu Arg
                245                 250                 255
Lys Met Thr Lys Glu Leu Gly Val Leu Trp Ile Asn Asp Glu Val Leu
            260                 265                 270
Thr Gly Phe Gly Arg Thr Gly Lys Trp Phe Gly Tyr Gln His Tyr Gly
        275                 280                 285
Val Gln Pro Asp Ile Ile Thr Met Gly Lys Gly Leu Ser Ser Ser Ser
    290                 295                 300
Leu Pro Ala Gly Ala Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
Ala Met Ala Ala Val Cys Ala Asn Leu Glu Val Met Met Glu Glu Asn
            340                 345                 350
Leu Val Glu Gln Ala Lys Asn Ser Gly Glu Tyr Ile Arg Ser Lys Leu
        355                 360                 365
Glu Leu Leu Gln Glu Lys His Lys Ser Ile Gly Asn Phe Asp Gly Tyr
    370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Thr His Gly Met Asn Pro Asn Gln
```

```
                405                 410                 415
Ile Pro Thr Gln Ile Ile Met Lys Lys Ala Leu Glu Lys Gly Val Leu
                420                 425                 430

Ile Gly Gly Val Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 6
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 6

Met Gly Leu Thr Val Gln Lys Ile Asn Trp Glu Gln Val Lys Glu Trp
1               5                   10                  15

Asp Arg Lys Tyr Leu Met Arg Thr Asp Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285
```

```
Val Gln Pro Asp Ile Ile Thr Met Gly Lys Gly Leu Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 7
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 7

```
Met Gly Leu Thr Val Gln Lys Ile Asn Trp Glu Gln Val Lys Glu Trp
1               5                   10                  15

Asp Arg Lys Tyr Leu Met Arg Thr Glu Ser Thr Gln Asn Glu Tyr Gln
                20                  25                  30

Pro Val Pro Ile Glu Ser Thr Glu Gly Asp Tyr Leu Ile Met Pro Gly
                35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
                130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175
```

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 8
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 8

Met Gly Leu Thr Val Gln Lys Ile Asn Trp Glu Gln Val Lys Glu Trp
1               5                   10                  15

Asp Arg Lys Tyr Leu Met Arg Thr His Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu

```
            50                  55                  60
Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                     85                  90                  95

Ala Ala Lys Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460

Leu Asp Tyr Leu Glu Ser Gly Glu Trp Gln Gln Ser
465                 470                 475
```

<210> SEQ ID NO 9
<211> LENGTH: 476
<212> TYPE: PRT
<213> ORGANISM: Artificial Sequence
<220> FEATURE:
<223> OTHER INFORMATION: engineered amine transaminase (ATA) based on ATA of Arthrobacter citreus

<400> SEQUENCE: 9

```
Met Gly Leu Thr Val Gln Lys Ile Asn Trp Glu Gln Val Lys Glu Trp
1               5                   10                  15

Asp Arg Lys Tyr Leu Met Arg Thr Lys Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
```

```
                355                 360                 365
Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 10
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 10

Met Gly Leu Thr Val Gln Lys Ile Asn Trp Glu Gln Val Lys Glu Trp
1               5                   10                  15

Asp Arg Lys Tyr Leu Met Arg Thr Arg Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240
```

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 11
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 11

Met Gly Leu Thr Val Gln Lys Ile Asn Trp Glu Gln Val Lys Glu Trp
1               5                   10                  15

Asp Arg Lys Tyr Leu Met Arg Thr Asn Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
            130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 12
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 12

Met Gly Leu Thr Val Gln Lys Ile Asn Trp Glu Gln Val Lys Glu Trp

-continued

```
1               5                   10                  15
Asp Arg Lys Tyr Leu Met Arg Thr Gln Ser Thr Gln Asn Glu Tyr Gln
            20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
            50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                    85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                    165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                    245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
            290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                    325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                    405                 410                 415

Ile Pro Thr Gln Ile Ile Met Glu Lys Ala Leu Glu Lys Gly Val Leu
                420                 425                 430
```

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 13
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 13

Met Gly Leu Thr Val Gln Lys Ile Asn Trp Glu Gln Val Lys Glu Trp
1               5                   10                  15

Asp Arg Lys Tyr Leu Met Arg Thr Ser Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met

```
                305                 310                 315                 320
Asp Lys His Arg Trp Glu Ser Val Ser Thr Tyr Ala Gly His Pro Val
                    325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                    405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 14
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 14

Met Gly Leu Thr Val Gln Lys Ile Asn Trp Glu Gln Val Lys Glu Trp
1               5                   10                  15

Asp Arg Lys Tyr Leu Met Arg Thr Thr Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190
```

```
Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 15
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 15

Met Gly Leu Thr Val Gln Lys Ile Asn Trp Glu Gln Val Lys Glu Trp
1               5                   10                  15

Asp Arg Lys Tyr Leu Met Arg Thr Cys Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80
```

Arg Tyr Gly Phe Val Trp Asp Thr Tyr Ala Thr Asp Tyr Lys Ala Lys
                    85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 16
<211> LENGTH: 476

```
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 16
```

Met Gly Leu Thr Val Gln Lys Ile Asn Trp Glu Gln Val Lys Glu Trp
1               5                   10                  15

Asp Arg Lys Tyr Leu Met Arg Thr Gly Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 17
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 17

Met Gly Leu Thr Val Gln Lys Ile Asn Trp Glu Gln Val Lys Glu Trp
1               5                   10                  15

Asp Arg Lys Tyr Leu Met Arg Thr Pro Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu

```
                260                 265                 270
Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 18
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 18

Met Gly Leu Thr Val Gln Lys Ile Asn Trp Glu Gln Val Lys Glu Trp
1               5                   10                  15

Asp Arg Lys Tyr Leu Met Arg Thr Ala Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140
```

```
Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 19
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 19

Met Gly Leu Thr Val Gln Lys Ile Asn Trp Glu Gln Val Lys Glu Trp
1               5                   10                  15

Asp Arg Lys Tyr Leu Met Arg Thr Ile Ser Thr Gln Asn Glu Tyr Gln
                20                  25                  30
```

```
Pro Val Pro Ile Glu Ser Thr Glu Gly Asp Tyr Leu Ile Met Pro Gly
         35                  40                  45

Gly Thr Arg Leu Leu Asp Phe Phe Asn Gln Leu Tyr Cys Val Asn Leu
     50                  55                  60

Gly Gln Lys Asn Gln Lys Val Asn Ala Ala Ile Lys Glu Ala Leu Asp
 65              70                  75                      80

Arg Tyr Gly Phe Val Trp Asp Thr Tyr Ala Thr Asp Tyr Lys Ala Lys
                 85                  90                  95

Ala Ala Lys Ile Ile Ile Glu Asp Ile Leu Gly Asp Glu Asp Trp Pro
            100             105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145             150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
    355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445
```

```
Val Ser Arg Gly Asp Ile Asp Lys Ala Met Asp Ala Leu Asp Tyr Ala
    450                 455                 460
Leu Asp Tyr Leu Glu Ser Gly Glu Trp Gln Gln Ser
465                 470                 475

<210> SEQ ID NO 20
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 20

Met Gly Leu Thr Val Gln Lys Ile Asn Trp Glu Gln Val Lys Glu Trp
1               5                   10                  15
Asp Arg Lys Tyr Leu Met Arg Thr Leu Ser Thr Gln Asn Glu Tyr Gln
                20                  25                  30
Pro Val Pro Ile Glu Ser Thr Glu Gly Asp Tyr Leu Ile Met Pro Gly
            35                  40                  45
Gly Thr Arg Leu Leu Asp Phe Phe Asn Gln Leu Tyr Cys Val Asn Leu
        50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
        115                 120                 125
Leu Asn Ile Ala Arg Leu Tyr Thr Asn Arg Pro Leu Val Val Thr Arg
    130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
    210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Leu Arg
                245                 250                 255
Lys Met Thr Lys Glu Leu Gly Val Leu Trp Ile Ala Asp Glu Val Leu
            260                 265                 270
Thr Gly Phe Gly Arg Thr Gly Lys Trp Phe Gly Tyr Gln His Tyr Gly
        275                 280                 285
Val Gln Pro Asp Ile Ile Thr Met Gly Lys Gly Leu Ser Ser Ser Ser
    290                 295                 300
Leu Pro Ala Gly Ala Val Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
```

```
Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 21
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 21

Met Gly Leu Thr Val Gln Lys Ile Asn Trp Glu Gln Val Lys Glu Trp
1               5                   10                  15

Asp Arg Lys Tyr Leu Met Arg Thr Met Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
```

```
            210                 215                 220
Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
            245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 22
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 22

Met Gly Leu Thr Val Gln Lys Ile Asn Trp Glu Gln Val Lys Glu Trp
1               5                   10                  15

Asp Arg Lys Tyr Leu Met Arg Thr Val Ser Thr Gln Asn Glu Tyr Gln
            20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65              70                  75                  80

Arg Tyr Gly Phe Val Trp Asp Thr Tyr Ala Thr Asp Tyr Lys Ala Lys
            85                  90                  95
```

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 23
<211> LENGTH: 476
<212> TYPE: PRT
<213> ORGANISM: Artificial Sequence
<220> FEATURE:
<223> OTHER INFORMATION: engineered amine transaminase (ATA) based on ATA of Arthrobacter citreus

<400> SEQUENCE: 23

```
Met Gly Leu Thr Val Gln Lys Ile Asn Trp Glu Gln Val Lys Glu Trp
1               5                   10                  15
Asp Arg Lys Tyr Leu Met Arg Thr Trp Ser Thr Gln Asn Glu Tyr Gln
            20                  25                  30
Pro Val Pro Ile Glu Ser Thr Glu Gly Asp Tyr Leu Ile Met Pro Gly
        35                  40                  45
Gly Thr Arg Leu Leu Asp Phe Phe Asn Gln Leu Tyr Cys Val Asn Leu
    50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
        115                 120                 125
Leu Asn Ile Ala Arg Leu Tyr Thr Asn Arg Pro Leu Val Val Thr Arg
    130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
    210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Leu Arg
                245                 250                 255
Lys Met Thr Lys Glu Leu Gly Val Leu Trp Ile Ala Asp Glu Val Leu
            260                 265                 270
Thr Gly Phe Gly Arg Thr Gly Lys Trp Phe Gly Tyr Gln His Tyr Gly
        275                 280                 285
Val Gln Pro Asp Ile Ile Thr Met Gly Lys Gly Leu Ser Ser Ser Ser
    290                 295                 300
Leu Pro Ala Gly Ala Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
Ala Met Ala Ala Val Cys Ala Asn Leu Glu Val Met Met Glu Glu Asn
            340                 345                 350
Leu Val Glu Gln Ala Lys Asn Ser Gly Glu Tyr Ile Arg Ser Lys Leu
        355                 360                 365
Glu Leu Leu Gln Glu Lys His Lys Ser Ile Gly Asn Phe Asp Gly Tyr
    370                 375                 380
Gly Leu Leu Trp Ile Val Asp Ile Val Asn Ala Lys Thr Lys Thr Pro
385                 390                 395                 400
```

```
Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 24
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 24

Met Gly Leu Thr Val Gln Lys Ile Asn Trp Glu Gln Val Lys Glu Trp
1               5                   10                  15

Asp Arg Lys Tyr Leu Met Arg Thr Tyr Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285
```

```
Val Gln Pro Asp Ile Ile Thr Met Gly Lys Gly Leu Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 25
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 25

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
            130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
```

165                 170                 175
Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Asp Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 26
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 26

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

```
Gly Thr Arg Leu Leu Asp Phe Phe Asn Gln Leu Tyr Cys Val Asn Leu
 50                  55                  60

Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                 85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Glu Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
```

<210> SEQ ID NO 27
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 27

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile His Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 28
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 28

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

```
Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Lys Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460

Leu Asp Tyr Leu Glu Ser Gly Glu Trp Gln Gln Ser
465                 470                 475

<210> SEQ ID NO 29
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 29

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
```

115                 120                 125
Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Arg Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 30
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 30

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
        130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met Asp
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
```

```
                420             425             430
Ile Gly Gly Ala Met Pro Asn Thr Met Arg Ile Gly Ala Ser Leu Asn
            435                 440             445

Val Ser Arg Gly Asp Ile Asp Lys Ala Met Asp Ala Leu Asp Tyr Ala
450                 455             460

Leu Asp Tyr Leu Glu Ser Gly Glu Trp Gln Gln Ser
465                 470             475

<210> SEQ ID NO 31
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 31

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Gln Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
290                 295                 300
```

```
Leu Pro Ala Gly Ala Val Val Ser Lys Glu Ile Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 32
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 32

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190
```

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
            245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 33
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 33

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp

```
                65                  70                  75                  80
        Arg Tyr Gly Phe Val Trp Asp Thr Tyr Ala Thr Asp Tyr Lys Ala Lys
                            85                  90                  95

Ala Ala Lys Ile Ile Ile Glu Asp Ile Leu Gly Asp Glu Asp Trp Pro
                        100                 105                 110

Gly Lys Val Arg Phe Val Ser Thr Gly Ser Glu Ala Val Glu Thr Ala
                        115                 120                 125

Leu Asn Ile Ala Arg Leu Tyr Thr Asn Arg Pro Leu Val Thr Arg
                        130                 135                 140

Glu His Asp Tyr His Gly Trp Thr Gly Ala Ala Thr Val Thr Arg
        145                 150                 155                 160

Leu Arg Ser Phe Arg Ser Gly Leu Val Gly Glu Asn Ser Glu Ser Phe
                            165                 170                 175

Ser Ala Gln Ile Pro Gly Ser Ser Tyr Asn Ser Ala Val Leu Met Ala
                        180                 185                 190

Pro Ser Ser Asn Met Phe Gln Asp Ser Asn Gly Asn Cys Leu Lys Asp
                        195                 200                 205

Glu Asn Gly Glu Leu Leu Ser Val Lys Tyr Thr Arg Arg Met Ile Glu
                    210                 215                 220

Asn Tyr Gly Pro Glu Gln Val Ala Ala Val Ile Thr Glu Val Ser Gln
        225                 230                 235                 240

Gly Val Gly Ser Thr Met Pro Pro Tyr Glu Tyr Ile Pro Gln Leu Arg
                            245                 250                 255

Lys Met Thr Lys Glu Leu Gly Val Leu Trp Ile Thr Asp Glu Val Leu
                        260                 265                 270

Thr Gly Phe Gly Arg Thr Gly Lys Trp Phe Gly Tyr Gln His Tyr Gly
                    275                 280                 285

Val Gln Pro Asp Ile Ile Thr Met Gly Lys Gly Leu Ser Ser Ser Ser
                    290                 295                 300

Leu Pro Ala Gly Ala Val Val Ser Lys Glu Ile Ala Ala Phe Met
        305                 310                 315                 320

Asp Lys His Arg Trp Glu Ser Val Ser Thr Tyr Ala Gly His Pro Val
                            325                 330                 335

Ala Met Ala Ala Val Cys Ala Asn Leu Glu Val Met Met Glu Glu Asn
                        340                 345                 350

Leu Val Glu Gln Ala Lys Asn Ser Gly Glu Tyr Ile Arg Ser Lys Leu
                    355                 360                 365

Glu Leu Leu Gln Glu Lys His Lys Ser Ile Gly Asn Phe Asp Gly Tyr
                    370                 375                 380

Gly Leu Leu Trp Ile Val Asp Ile Val Asn Ala Lys Thr Lys Thr Pro
        385                 390                 395                 400

Tyr Val Lys Leu Asp Arg Asn Phe Arg His Gly Met Asn Pro Asn Gln
                            405                 410                 415

Ile Pro Thr Gln Ile Ile Met Glu Lys Ala Leu Glu Lys Gly Val Leu
                        420                 425                 430

Ile Gly Gly Ala Met Pro Asn Thr Met Arg Ile Gly Ala Ser Leu Asn
                    435                 440                 445

Val Ser Arg Gly Asp Ile Asp Lys Ala Met Asp Ala Leu Asp Tyr Ala
                    450                 455                 460

Leu Asp Tyr Leu Glu Ser Gly Glu Trp Gln Gln Ser
        465                 470                 475

<210> SEQ ID NO 34
```

<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 34

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Cys Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr

```
                  370                 375                 380
Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 35
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 35

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255
```

Lys Met Thr Lys Glu Leu Gly Val Leu Trp Ile Asp Glu Val Leu
             260                 265                 270

Thr Gly Phe Gly Arg Thr Gly Lys Trp Phe Gly Tyr Gln His Tyr Gly
             275                 280                 285

Val Gln Pro Asp Ile Ile Thr Met Gly Lys Gly Leu Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 36
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 36

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

```
Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Pro Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 37
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 37

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
```

```
                20                  25                  30
Pro Val Pro Ile Glu Ser Thr Glu Gly Asp Tyr Leu Ile Met Pro Gly
                35                  40                  45
Gly Thr Arg Leu Leu Asp Phe Phe Asn Gln Leu Tyr Cys Val Asn Leu
            50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
            115                 120                 125
Leu Asn Ile Ala Arg Leu Tyr Thr Asn Arg Pro Leu Val Val Thr Arg
            130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
            195                 200                 205
Glu Asn Gly Glu Leu Leu Ser Val Lys Tyr Thr Arg Arg Met Ile Glu
            210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Leu Arg
                245                 250                 255
Lys Met Thr Lys Glu Leu Gly Val Leu Trp Ile Phe Asp Glu Val Leu
            260                 265                 270
Thr Gly Phe Gly Arg Thr Gly Lys Trp Phe Gly Tyr Gln His Tyr Gly
            275                 280                 285
Val Gln Pro Asp Ile Ile Thr Met Gly Lys Gly Leu Ser Ser Ser Ser
            290                 295                 300
Leu Pro Ala Gly Ala Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
Ala Met Ala Ala Val Cys Ala Asn Leu Glu Val Met Met Glu Glu Asn
            340                 345                 350
Leu Val Glu Gln Ala Lys Asn Ser Gly Glu Tyr Ile Arg Ser Lys Leu
            355                 360                 365
Glu Leu Leu Gln Glu Lys His Lys Ser Ile Gly Asn Phe Asp Gly Tyr
            370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
            420                 425                 430
Ile Gly Gly Ala Met Pro Asn Thr Met Arg Ile Gly Ala Ser Leu Asn
            435                 440                 445
```

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 38
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 38

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val

```
                        325                 330                 335
Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 39
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 39

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205
```

Glu Asn Gly Glu Leu Leu Ser Val Lys Tyr Thr Arg Arg Met Ile Glu
        210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Leu Asp Glu Val Leu
        260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
        340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
        420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 40
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 40

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
        100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
        130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Met Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
        290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 41
<211> LENGTH: 476
<212> TYPE: PRT
<213> ORGANISM: Artificial Sequence
<220> FEATURE:

<223> OTHER INFORMATION: engineered amine transaminase (ATA) based on ATA of Arthrobacter citreus

<400> SEQUENCE: 41

| | | | | | | | | | | | | | | |
|---|---|---|---|---|---|---|---|---|---|---|---|---|---|---|
| Met | Gly | Leu | Thr | Val | Gln | Lys | Ile | Asn | Trp | Glu | Gln | Val | Lys | Glu | Trp |
| 1 | | | | 5 | | | | | 10 | | | | | 15 | |
| Asp | Arg | Lys | Tyr | Leu | Met | Arg | Thr | Phe | Ser | Thr | Gln | Asn | Glu | Tyr | Gln |
| | | | 20 | | | | | 25 | | | | | 30 | | |
| Pro | Val | Pro | Ile | Glu | Ser | Thr | Glu | Gly | Asp | Tyr | Leu | Ile | Met | Pro | Gly |
| | | 35 | | | | | 40 | | | | | 45 | | | |
| Gly | Thr | Arg | Leu | Leu | Asp | Phe | Phe | Asn | Gln | Leu | Tyr | Cys | Val | Asn | Leu |
| | 50 | | | | | 55 | | | | | 60 | | | | |
| Gly | Gln | Lys | Asn | Gln | Lys | Val | Asn | Ala | Ala | Ile | Lys | Glu | Ala | Leu | Asp |
| 65 | | | | | 70 | | | | | 75 | | | | | 80 |
| Arg | Tyr | Gly | Phe | Val | Trp | Asp | Thr | Tyr | Ala | Thr | Asp | Tyr | Lys | Ala | Lys |
| | | | | 85 | | | | | 90 | | | | | 95 | |
| Ala | Ala | Lys | Ile | Ile | Ile | Glu | Asp | Ile | Leu | Gly | Asp | Glu | Asp | Trp | Pro |
| | | | 100 | | | | | 105 | | | | | 110 | | |
| Gly | Lys | Val | Arg | Phe | Val | Ser | Thr | Gly | Ser | Glu | Ala | Val | Glu | Thr | Ala |
| | | 115 | | | | | 120 | | | | | 125 | | | |
| Leu | Asn | Ile | Ala | Arg | Leu | Tyr | Thr | Asn | Arg | Pro | Leu | Val | Val | Thr | Arg |
| | 130 | | | | | 135 | | | | | 140 | | | | |
| Glu | His | Asp | Tyr | His | Gly | Trp | Thr | Gly | Ala | Ala | Thr | Val | Thr | Arg | |
| 145 | | | | | 150 | | | | | 155 | | | | | 160 |
| Leu | Arg | Ser | Phe | Arg | Ser | Gly | Leu | Val | Gly | Glu | Asn | Ser | Glu | Ser | Phe |
| | | | | 165 | | | | | 170 | | | | | 175 | |
| Ser | Ala | Gln | Ile | Pro | Gly | Ser | Ser | Tyr | Asn | Ser | Ala | Val | Leu | Met | Ala |
| | | | 180 | | | | | 185 | | | | | 190 | | |
| Pro | Ser | Ser | Asn | Met | Phe | Gln | Asp | Ser | Asn | Gly | Asn | Cys | Leu | Lys | Asp |
| | | 195 | | | | | 200 | | | | | 205 | | | |
| Glu | Asn | Gly | Glu | Leu | Leu | Ser | Val | Lys | Tyr | Thr | Arg | Arg | Met | Ile | Glu |
| | 210 | | | | | 215 | | | | | 220 | | | | |
| Asn | Tyr | Gly | Pro | Glu | Gln | Val | Ala | Ala | Val | Ile | Thr | Glu | Val | Ser | Gln |
| 225 | | | | | 230 | | | | | 235 | | | | | 240 |
| Gly | Val | Gly | Ser | Thr | Met | Pro | Pro | Tyr | Glu | Tyr | Ile | Pro | Gln | Leu | Arg |
| | | | | 245 | | | | | 250 | | | | | 255 | |
| Lys | Met | Thr | Lys | Glu | Leu | Gly | Val | Leu | Trp | Ile | Val | Asp | Glu | Val | Leu |
| | | | 260 | | | | | 265 | | | | | 270 | | |
| Thr | Gly | Phe | Gly | Arg | Thr | Gly | Lys | Trp | Phe | Gly | Tyr | Gln | His | Tyr | Gly |
| | | 275 | | | | | 280 | | | | | 285 | | | |
| Val | Gln | Pro | Asp | Ile | Ile | Thr | Met | Gly | Lys | Gly | Leu | Ser | Ser | Ser | Ser |
| | 290 | | | | | 295 | | | | | 300 | | | | |
| Leu | Pro | Ala | Gly | Ala | Val | Val | Ser | Lys | Glu | Ile | Ala | Ala | Phe | Met | |
| 305 | | | | | 310 | | | | | 315 | | | | | 320 |
| Asp | Lys | His | Arg | Trp | Glu | Ser | Val | Ser | Thr | Tyr | Ala | Gly | His | Pro | Val |
| | | | | 325 | | | | | 330 | | | | | 335 | |
| Ala | Met | Ala | Ala | Val | Cys | Ala | Asn | Leu | Glu | Val | Met | Met | Glu | Glu | Asn |
| | | | 340 | | | | | 345 | | | | | 350 | | |
| Leu | Val | Glu | Gln | Ala | Lys | Asn | Ser | Gly | Glu | Tyr | Ile | Arg | Ser | Lys | Leu |
| | | 355 | | | | | 360 | | | | | 365 | | | |
| Glu | Leu | Leu | Gln | Glu | Lys | His | Lys | Ser | Ile | Gly | Asn | Phe | Asp | Gly | Tyr |
| | 370 | | | | | 375 | | | | | 380 | | | | |
| Gly | Leu | Leu | Trp | Ile | Val | Asp | Ile | Val | Asn | Ala | Lys | Thr | Lys | Thr | Pro |
| 385 | | | | | 390 | | | | | 395 | | | | | 400 |

```
Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 42
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 42

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
                35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
        130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Trp Asp Glu Val Leu
                260                 265                 270

Thr Gly Phe Gly Arg Thr Gly Lys Trp Phe Gly Tyr Gln His Tyr Gly
```

```
            275                 280                 285
Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 43
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 43

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160
```

Leu Arg Ser Phe Arg Ser Gly Leu Val Gly Glu Asn Ser Glu Ser Phe
            165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
        210                 215                 220

Asn Tyr Gly Pro Glu Gln Val Ala Ala Val Thr Glu Val Ser Gln
225                 230                 235                 240

Gly Val Gly Ser Thr Met Pro Pro Tyr Glu Tyr Ile Pro Gln Leu Arg
            245                 250                 255

Lys Met Thr Lys Glu Leu Gly Val Leu Trp Ile Tyr Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 44
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 44

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
            35                  40                  45

```
Gly Thr Arg Leu Leu Asp Phe Phe Asn Gln Leu Tyr Cys Val Asn Leu
 50                  55                  60

Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                 85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
            130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
            210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Asp Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460
```

-continued

Leu Asp Tyr Leu Glu Ser Gly Glu Trp Gln Gln Ser
465                 470                 475

<210> SEQ ID NO 45
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 45

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Glu Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 46
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 46

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln

| | | | | | | | | | | | |
|---|---|---|---|---|---|---|---|---|---|---|---|
| 225 | | | | 230 | | | | 235 | | | 240 |

Gly Val Gly Ser Thr Met Pro Pro Tyr Glu Tyr Ile Pro Gln Leu Arg
             245                          250                        255

Lys Met Thr Lys Glu Leu Gly Val Leu Trp Ile Ala Asp Glu Val Leu
          260                         265                      270

Thr Gly Phe Gly Arg Thr Gly Lys Trp Phe Gly Tyr Gln His Tyr Gly
         275                         280                    285

Val Gln Pro Asp Ile Ile Thr Met Gly Lys Gly Leu Ser Ser Ser Ser
    290                       295                    300

Leu Pro Ala Gly Ala Val Val Ser Lys Glu Ile Ala Ala Phe Met
305                    310                    315                  320

Asp Lys His Arg Trp Glu Ser His Ser Thr Tyr Ala Gly His Pro Val
             325                        330                   335

Ala Met Ala Ala Val Cys Ala Asn Leu Glu Val Met Met Glu Glu Asn
          340                       345                   350

Leu Val Glu Gln Ala Lys Asn Ser Gly Glu Tyr Ile Arg Ser Lys Leu
         355                         360                    365

Glu Leu Leu Gln Glu Lys His Lys Ser Ile Gly Asn Phe Asp Gly Tyr
    370                       375                    380

Gly Leu Leu Trp Ile Val Asp Ile Val Asn Ala Lys Thr Lys Thr Pro
385                    390                    395                  400

Tyr Val Lys Leu Asp Arg Asn Phe Arg His Gly Met Asn Pro Asn Gln
             405                        410                   415

Ile Pro Thr Gln Ile Ile Met Glu Lys Ala Leu Glu Lys Gly Val Leu
            420                       425                    430

Ile Gly Gly Ala Met Pro Asn Thr Met Arg Ile Gly Ala Ser Leu Asn
         435                         440                    445

Val Ser Arg Gly Asp Ile Asp Lys Ala Met Asp Ala Leu Asp Tyr Ala
          450                       455                   460

Leu Asp Tyr Leu Glu Ser Gly Glu Trp Gln Gln Ser
465                    470                    475

<210> SEQ ID NO 47
<211> LENGTH: 476
<212> TYPE: PRT
<213> ORGANISM: Artificial Sequence
<220> FEATURE:
<223> OTHER INFORMATION: engineered amine transaminase (ATA) based on
     ATA of Arthrobacter citreus

<400> SEQUENCE: 47

Met Gly Leu Thr Val Gln Lys Ile Asn Trp Glu Gln Val Lys Glu Trp
1                 5                    10                  15

Asp Arg Lys Tyr Leu Met Arg Thr Phe Ser Thr Gln Asn Glu Tyr Gln
          20                       25                    30

Pro Val Pro Ile Glu Ser Thr Glu Gly Asp Tyr Leu Ile Met Pro Gly
         35                         40                    45

Gly Thr Arg Leu Leu Asp Phe Phe Asn Gln Leu Tyr Cys Val Asn Leu
    50                       55                    60

Gly Gln Lys Asn Gln Lys Val Asn Ala Ala Ile Lys Glu Ala Leu Asp
65                    70                    75                  80

Arg Tyr Gly Phe Val Trp Asp Thr Tyr Ala Thr Asp Tyr Lys Ala Lys
         85                         90                    95

Ala Ala Lys Ile Ile Ile Glu Asp Ile Leu Gly Asp Glu Asp Trp Pro
          100                       105                  110

Gly Lys Val Arg Phe Val Ser Thr Gly Ser Glu Ala Val Glu Thr Ala
            115                 120                 125
Leu Asn Ile Ala Arg Leu Tyr Thr Asn Arg Pro Leu Val Val Thr Arg
        130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Leu Arg
                245                 250                 255
Lys Met Thr Lys Glu Leu Gly Val Leu Trp Ile Ala Asp Glu Val Leu
            260                 265                 270
Thr Gly Phe Gly Arg Thr Gly Lys Trp Phe Gly Tyr Gln His Tyr Gly
        275                 280                 285
Val Gln Pro Asp Ile Ile Thr Met Gly Lys Gly Leu Ser Ser Ser Ser
        290                 295                 300
Leu Pro Ala Gly Ala Val Val Ser Lys Glu Ile Ala Ala Phe Met
305                 310                 315                 320
Asp Lys His Arg Trp Glu Ser Lys Ser Thr Tyr Ala Gly His Pro Val
                325                 330                 335
Ala Met Ala Ala Val Cys Ala Asn Leu Glu Val Met Met Glu Glu Asn
            340                 345                 350
Leu Val Glu Gln Ala Lys Asn Ser Gly Glu Tyr Ile Arg Ser Lys Leu
        355                 360                 365
Glu Leu Leu Gln Glu Lys His Lys Ser Ile Gly Asn Phe Asp Gly Tyr
370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
            420                 425                 430
Ile Gly Gly Ala Met Pro Asn Thr Met Arg Ile Gly Ala Ser Leu Asn
        435                 440                 445
Val Ser Arg Gly Asp Ile Asp Lys Ala Met Asp Ala Leu Asp Tyr Ala
450                 455                 460
Leu Asp Tyr Leu Glu Ser Gly Glu Trp Gln Gln Ser
465                 470                 475

<210> SEQ ID NO 48
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 48

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Arg Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415
```

```
Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 49
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 49

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300
```

```
Leu Pro Ala Gly Ala Val Val Ser Lys Glu Ile Ala Ala Phe Met
305                 310                 315                 320

Asp Lys His Arg Trp Glu Ser Asn Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 50
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 50

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175
```

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Gln Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 51
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 51

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu

-continued

```
                50                  55                  60
Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                     85                  90                  95

Ala Ala Lys Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Ser Lys Glu Ile Ala Ala Phe Met
305                 310                 315                 320

Asp Lys His Arg Trp Glu Ser Ser Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460

Leu Asp Tyr Leu Glu Ser Gly Glu Trp Gln Gln Ser
465                 470                 475
```

<210> SEQ ID NO 52
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 52

```
Met Gly Leu Thr Val Gln Lys Ile Asn Trp Glu Gln Val Lys Glu Trp
1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Thr Ser Thr Tyr Ala Gly His Pro Val
                325                 330                 335

Ala Met Ala Ala Val Cys Ala Asn Leu Glu Val Met Met Glu Glu Asn
            340                 345                 350
```

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 53
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 53

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln

```
                     225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Ser Lys Glu Ile Ala Ala Phe Met
305                 310                 315                 320

Asp Lys His Arg Trp Glu Ser Cys Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460

Leu Asp Tyr Leu Glu Ser Gly Glu Trp Gln Gln Ser
465                 470                 475

<210> SEQ ID NO 54
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 54

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
                35                  40                  45

Gly Thr Arg Leu Leu Asp Phe Phe Asn Gln Leu Tyr Cys Val Asn Leu
            50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110
```

```
Gly Lys Val Arg Phe Val Ser Thr Gly Ser Glu Ala Val Glu Thr Ala
            115                 120                 125
Leu Asn Ile Ala Arg Leu Tyr Thr Asn Arg Pro Leu Val Val Thr Arg
        130                 135                 140
Glu His Asp Tyr His Gly Trp Thr Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Leu Arg
                245                 250                 255
Lys Met Thr Lys Glu Leu Gly Val Leu Trp Ile Ala Asp Glu Val Leu
            260                 265                 270
Thr Gly Phe Gly Arg Thr Gly Lys Trp Phe Gly Tyr Gln His Tyr Gly
        275                 280                 285
Val Gln Pro Asp Ile Ile Thr Met Gly Lys Gly Leu Ser Ser Ser Ser
        290                 295                 300
Leu Pro Ala Gly Ala Val Val Ser Lys Glu Ile Ala Ala Phe Met
305                 310                 315                 320
Asp Lys His Arg Trp Glu Ser Gly Ser Thr Tyr Ala Gly His Pro Val
                325                 330                 335
Ala Met Ala Ala Val Cys Ala Asn Leu Glu Val Met Met Glu Glu Asn
            340                 345                 350
Leu Val Glu Gln Ala Lys Asn Ser Gly Glu Tyr Ile Arg Ser Lys Leu
        355                 360                 365
Glu Leu Leu Gln Glu Lys His Lys Ser Ile Gly Asn Phe Asp Gly Tyr
    370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
            420                 425                 430
Ile Gly Gly Ala Met Pro Asn Thr Met Arg Ile Gly Ala Ser Leu Asn
        435                 440                 445
Val Ser Arg Gly Asp Ile Asp Lys Ala Met Asp Ala Leu Asp Tyr Ala
    450                 455                 460
Leu Asp Tyr Leu Glu Ser Gly Glu Trp Gln Gln Ser
465                 470                 475
```

<210> SEQ ID NO 55
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 55

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Pro Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
```

```
                    405                 410                 415
Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 56
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 56

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285
```

```
Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Ala Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 57
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 57

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160
```

Leu Arg Ser Phe Arg Ser Gly Leu Val Gly Glu Asn Ser Glu Ser Phe
            165                 170                 175

Ser Ala Gln Ile Pro Gly Ser Ser Tyr Asn Ser Ala Val Leu Met Ala
        180                 185                 190

Pro Ser Ser Asn Met Phe Gln Asp Ser Asn Gly Asn Cys Leu Lys Asp
    195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
            245                 250                 255

Lys Met Thr Lys Glu Leu Gly Val Leu Trp Ile Ala Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Phe Ser Thr Tyr Ala Gly His Pro Val
            325                 330                 335

Ala Met Ala Ala Val Cys Ala Asn Leu Glu Val Met Met Glu Glu Asn
        340                 345                 350

Leu Val Glu Gln Ala Lys Asn Ser Gly Glu Tyr Ile Arg Ser Lys Leu
    355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
        420                 425                 430

Ile Gly Gly Ala Met Pro Asn Thr Met Arg Ile Gly Ala Ser Leu Asn
    435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 58
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 58

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly

```
                35                  40                  45
Gly Thr Arg Leu Leu Asp Phe Phe Asn Gln Leu Tyr Cys Val Asn Leu
 50                  55                  60

Gly Gln Lys Asn Gln Lys Val Asn Ala Ala Ile Lys Glu Ala Leu Asp
 65                  70                  75                  80

Arg Tyr Gly Phe Val Trp Asp Thr Tyr Thr Asp Tyr Lys Ala Lys
                 85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
                210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Ile Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460
```

Leu Asp Tyr Leu Glu Ser Gly Glu Trp Gln Gln Ser
465                 470                 475

<210> SEQ ID NO 59
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus (ATA) based on ATA of Arthrobacter
      citreus

<400> SEQUENCE: 59

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Leu Ser Thr Tyr Ala Gly His Pro Val
                325                 330                 335

```
Ala Met Ala Ala Val Cys Ala Asn Leu Glu Val Met Met Glu Asn
                340                 345                 350
Leu Val Glu Gln Ala Lys Asn Ser Gly Glu Tyr Ile Arg Ser Lys Leu
                355                 360                 365
Glu Leu Leu Gln Glu Lys His Lys Ser Ile Gly Asn Phe Asp Gly Tyr
            370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
                420                 425                 430
Ile Gly Gly Ala Met Pro Asn Thr Met Arg Ile Gly Ala Ser Leu Asn
            435                 440                 445
Val Ser Arg Gly Asp Ile Asp Lys Ala Met Asp Ala Leu Asp Tyr Ala
            450                 455                 460
Leu Asp Tyr Leu Glu Ser Gly Glu Trp Gln Gln Ser
465                 470                 475

<210> SEQ ID NO 60
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 60

Met Gly Leu Thr Val Gln Lys Ile Asn Trp Glu Gln Val Lys Glu Trp
1               5                   10                  15
Asp Arg Lys Tyr Leu Met Arg Thr Phe Ser Thr Gln Asn Glu Tyr Gln
                20                  25                  30
Pro Val Pro Ile Glu Ser Thr Glu Gly Asp Tyr Leu Ile Met Pro Gly
            35                  40                  45
Gly Thr Arg Leu Leu Asp Phe Phe Asn Gln Leu Tyr Cys Val Asn Leu
        50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
            100                 105                 110
Gly Lys Val Arg Phe Val Ser Thr Gly Ser Glu Ala Val Glu Thr Ala
        115                 120                 125
Leu Asn Ile Ala Arg Leu Tyr Thr Asn Arg Pro Leu Val Val Thr Arg
    130                 135                 140
Glu His Asp Tyr His Gly Trp Thr Gly Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
            180                 185                 190
Pro Ser Ser Asn Met Phe Gln Asp Ser Asn Gly Asn Cys Leu Lys Asp
        195                 200                 205
Glu Asn Gly Glu Leu Leu Ser Val Lys Tyr Thr Arg Arg Met Ile Glu
    210                 215                 220
```

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
            245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Met Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 61
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 61

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
            85                  90                  95

Ala Ala Lys Ile Ile Ile Glu Asp Ile Leu Gly Asp Glu Asp Trp Pro

```
            100                 105                  110
Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
                210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Ser Lys Glu Ile Ala Ala Phe Met
305                 310                 315                 320

Asp Lys His Arg Trp Glu Ser Trp Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 62
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus
```

<400> SEQUENCE: 62

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Leu Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Tyr Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
```

```
                    405                 410                 415
Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 63
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 63

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Asp Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285
```

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 64
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 64

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
                35                  40                  45

Gly Thr Arg Leu Leu Asp Phe Phe Asn Gln Leu Tyr Cys Val Asn Leu
            50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

```
Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Glu Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 65
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 65

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
```

```
            50                  55                  60
Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                     85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Asn Ser Glu Ser Phe
                    165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln His Arg
                    245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
    355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 66
<211> LENGTH: 476
<212> TYPE: PRT
<213> ORGANISM: Artificial Sequence
<220> FEATURE:
<223> OTHER INFORMATION: engineered amine transaminase (ATA) based on ATA of Arthrobacter citreus

<400> SEQUENCE: 66

```
Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Lys Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
```

```
                355                 360                 365
Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 67
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 67

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240
```

```
Gly Val Gly Ser Thr Met Pro Pro Tyr Glu Tyr Ile Pro Gln Arg Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
            290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 68
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 68

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125
```

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Asn Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 69
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 69

Met Gly Leu Thr Val Gln Lys Ile Asn Trp Glu Gln Val Lys Glu Trp

-continued

```
1               5                   10                  15
Asp Arg Lys Tyr Leu Met Arg Thr Phe Ser Thr Gln Asn Glu Tyr Gln
                20                  25                  30
Pro Val Pro Ile Glu Ser Thr Glu Gly Asp Tyr Leu Ile Met Pro Gly
                35                  40                  45
Gly Thr Arg Leu Leu Asp Phe Phe Asn Gln Leu Tyr Cys Val Asn Leu
            50                  55                  60
Gly Gln Lys Asn Gln Lys Val Asn Ala Ala Ile Lys Glu Ala Leu Asp
65                  70                  75                  80
Arg Tyr Gly Phe Val Trp Asp Thr Tyr Ala Thr Asp Tyr Lys Ala Lys
                85                  90                  95
Ala Ala Lys Ile Ile Ile Glu Asp Ile Leu Gly Asp Glu Asp Trp Pro
                100                 105                 110
Gly Lys Val Arg Phe Val Ser Thr Gly Ser Glu Ala Val Glu Thr Ala
                115                 120                 125
Leu Asn Ile Ala Arg Leu Tyr Thr Asn Arg Pro Leu Val Val Thr Arg
                130                 135                 140
Glu His Asp Tyr His Gly Trp Thr Gly Gly Ala Ala Thr Val Thr Arg
145                 150                 155                 160
Leu Arg Ser Phe Arg Ser Gly Leu Val Gly Glu Asn Ser Glu Ser Phe
                165                 170                 175
Ser Ala Gln Ile Pro Gly Ser Ser Tyr Asn Ser Ala Val Leu Met Ala
                180                 185                 190
Pro Ser Ser Asn Met Phe Gln Asp Ser Asn Gly Asn Cys Leu Lys Asp
                195                 200                 205
Glu Asn Gly Glu Leu Leu Ser Val Lys Tyr Thr Arg Arg Met Ile Glu
                210                 215                 220
Asn Tyr Gly Pro Glu Gln Val Ala Ala Val Ile Thr Glu Val Ser Gln
225                 230                 235                 240
Gly Val Gly Ser Thr Met Pro Pro Tyr Glu Tyr Ile Pro Gln Gln Arg
                245                 250                 255
Lys Met Thr Lys Glu Leu Gly Val Leu Trp Ile Ala Asp Glu Val Leu
                260                 265                 270
Thr Gly Phe Gly Arg Thr Gly Lys Trp Phe Gly Tyr Gln His Tyr Gly
                275                 280                 285
Val Gln Pro Asp Ile Ile Thr Met Gly Lys Gly Leu Ser Ser Ser Ser
                290                 295                 300
Leu Pro Ala Gly Ala Val Val Val Ser Lys Glu Ile Ala Ala Phe Met
305                 310                 315                 320
Asp Lys His Arg Trp Glu Ser Val Ser Thr Tyr Ala Gly His Pro Val
                325                 330                 335
Ala Met Ala Ala Val Cys Ala Asn Leu Glu Val Met Met Glu Glu Asn
                340                 345                 350
Leu Val Glu Gln Ala Lys Asn Ser Gly Glu Tyr Ile Arg Ser Lys Leu
                355                 360                 365
Glu Leu Leu Gln Glu Lys His Lys Ser Ile Gly Asn Phe Asp Gly Tyr
                370                 375                 380
Gly Leu Leu Trp Ile Val Asp Ile Val Asn Ala Lys Thr Lys Thr Pro
385                 390                 395                 400
Tyr Val Lys Leu Asp Arg Asn Phe Arg His Gly Met Asn Pro Asn Gln
                405                 410                 415
Ile Pro Thr Gln Ile Ile Met Glu Lys Ala Leu Glu Lys Gly Val Leu
                420                 425                 430
```

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 70
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 70

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Ser Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met

```
                    305                 310                 315                 320
Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
                370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445

Val Ser Arg Gly Asp Ile Asp Lys Ala Met Asp Ala Leu Asp Tyr Ala
                450                 455                 460

Leu Asp Tyr Leu Glu Ser Gly Glu Trp Gln Gln Ser
465                 470                 475

<210> SEQ ID NO 71
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 71

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
                35                  40                  45

Gly Thr Arg Leu Leu Asp Phe Phe Asn Gln Leu Tyr Cys Val Asn Leu
                50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
                130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190
```

```
Pro Ser Ser Asn Met Phe Gln Asp Ser Asn Gly Asn Cys Leu Lys Asp
            195                 200                 205

Glu Asn Gly Glu Leu Leu Ser Val Lys Tyr Thr Arg Arg Met Ile Glu
        210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Thr Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 72
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 72

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80
```

Arg Tyr Gly Phe Val Trp Asp Thr Tyr Ala Thr Asp Tyr Lys Ala Lys
                85                  90                  95

Ala Ala Lys Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
            115                 120                 125

Leu Asn Ile Ala Arg Leu Tyr Thr Asn Arg Pro Leu Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
            210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Cys Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
450                 455                 460

Leu Asp Tyr Leu Glu Ser Gly Glu Trp Gln Gln Ser
465                 470                 475

<210> SEQ ID NO 73
<211> LENGTH: 476

<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 73

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Gly Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380
```

```
Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475
```

<210> SEQ ID NO 74
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 74

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Pro Arg
                245                 250                 255

Lys Met Thr Lys Glu Leu Gly Val Leu Trp Ile Ala Asp Glu Val Leu
```

```
                 260                 265                 270
Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
            370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 75
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 75

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140
```

Glu His Asp Tyr His Gly Trp Thr Gly Gly Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Ala Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
            275                 280                 285

Val Gln Pro Asp Ile Ile Thr Met Gly Lys Gly Leu Ser Ser Ser Ser
        290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
        370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
        450                 455                 460

Leu Asp Tyr Leu Glu Ser Gly Glu Trp Gln Gln Ser
465                 470                 475

<210> SEQ ID NO 76
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 76

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

```
Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
 50                  55                  60

Gly Gln Lys Asn Gln Lys Val Asn Ala Ala Ile Lys Glu Ala Leu Asp
 65                  70                  75                  80

Arg Tyr Gly Phe Val Trp Asp Thr Tyr Ala Thr Asp Tyr Lys Ala Lys
                 85                  90                  95

Ala Ala Lys Ile Ile Ile Glu Asp Ile Leu Gly Asp Glu Asp Trp Pro
                100                 105                 110

Gly Lys Val Arg Phe Val Ser Thr Gly Ser Glu Ala Val Glu Thr Ala
                115                 120                 125

Leu Asn Ile Ala Arg Leu Tyr Thr Asn Arg Pro Leu Val Val Thr Arg
130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
                180                 185                 190

Pro Ser Ser Asn Met Phe Gln Asp Ser Asn Gly Asn Cys Leu Lys Asp
                195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Phe Arg
                245                 250                 255

Lys Met Thr Lys Glu Leu Gly Val Leu Trp Ile Ala Asp Glu Val Leu
                260                 265                 270

Thr Gly Phe Gly Arg Thr Gly Lys Trp Phe Gly Tyr Gln His Tyr Gly
                275                 280                 285

Val Gln Pro Asp Ile Ile Thr Met Gly Lys Gly Leu Ser Ser Ser Ser
                290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
                340                 345                 350

Leu Val Glu Gln Ala Lys Asn Ser Gly Glu Tyr Ile Arg Ser Lys Leu
                355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
                420                 425                 430

Ile Gly Gly Ala Met Pro Asn Thr Met Arg Ile Gly Ala Ser Leu Asn
                435                 440                 445
```

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 77
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 77

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Ile Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

```
Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 78
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 78

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
```

```
                210                 215                 220
Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Met Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 79
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 79

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95
```

```
Ala Ala Lys Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Val Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475

<210> SEQ ID NO 80
<211> LENGTH: 476
<212> TYPE: PRT
<213> ORGANISM: Artificial Sequence
<220> FEATURE:
<223> OTHER INFORMATION: engineered amine transaminase (ATA) based on
```

ATA of Arthrobacter citreus

<400> SEQUENCE: 80

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Trp Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400
```

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
            450                 455                 460

Leu Asp Tyr Leu Glu Ser Gly Glu Trp Gln Gln Ser
465                 470                 475

<210> SEQ ID NO 81
<211> LENGTH: 476
<212> TYPE: PRT
<213> ORGANISM: Artificial Sequence
<220> FEATURE:
<223> OTHER INFORMATION: engineered amine transaminase (ATA) based on
      ATA of Arthrobacter citreus

<400> SEQUENCE: 81

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Met Pro Gly
            35                  40                  45

Gly Thr Arg Leu Leu Asp Phe Phe Asn Gln Leu Tyr Cys Val Asn Leu
        50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Ser Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Tyr Arg
                245                 250                 255

Lys Met Thr Lys Glu Leu Gly Val Leu Trp Ile Ala Asp Glu Val Leu
            260                 265                 270

Thr Gly Phe Gly Arg Thr Gly Lys Trp Phe Gly Tyr Gln His Tyr Gly
        275                 280                 285

```
Val Gln Pro Asp Ile Ile Thr Met Gly Lys Gly Leu Ser Ser Ser
    290             295             300

Leu Pro Ala Gly Ala Val Val Ser Lys Glu Ile Ala Ala Phe Met
305             310             315                 320

Asp Lys His Arg Trp Glu Ser Val Ser Thr Tyr Ala Gly His Pro Val
            325             330             335

Ala Met Ala Ala Val Cys Ala Asn Leu Glu Val Met Met Glu Glu Asn
            340             345             350

Leu Val Glu Gln Ala Lys Asn Ser Gly Glu Tyr Ile Arg Ser Lys Leu
        355             360             365

Glu Leu Leu Gln Glu Lys His Lys Ser Ile Gly Asn Phe Asp Gly Tyr
    370             375             380

Gly Leu Leu Trp Ile Val Asp Ile Val Asn Ala Lys Thr Lys Thr Pro
385             390             395             400

Tyr Val Lys Leu Asp Arg Asn Phe Arg His Gly Met Asn Pro Asn Gln
            405             410             415

Ile Pro Thr Gln Ile Ile Met Glu Lys Ala Leu Glu Lys Gly Val Leu
            420             425             430

Ile Gly Gly Ala Met Pro Asn Thr Met Arg Ile Gly Ala Ser Leu Asn
        435             440             445

Val Ser Arg Gly Asp Ile Asp Lys Ala Met Asp Ala Leu Asp Tyr Ala
    450             455             460

Leu Asp Tyr Leu Glu Ser Gly Glu Trp Gln Gln Ser
465             470             475
```